United States Patent [19]

van Ooijen et al.

[11] Patent Number: 5,543,576
[45] Date of Patent: Aug. 6, 1996

[54] PRODUCTION OF ENZYMES IN SEEDS AND THEIR USE

[75] Inventors: Albert J. J. van Ooijen, Voorburg; Krijn Rietveld, Vlaardingen; Andreas Hoekema, Oegstgeest; Jan Pen, Leiden; Peter C. Sijmons, Amsterdam; Teunis C. Verwoerd, Leiden; Wilhemus J. Quax, Voorschoten, all of Netherlands

[73] Assignees: Mogen International, Leiden; Gist-Brocades, Delft, both of Netherlands

[21] Appl. No.: 146,422

[22] Filed: Nov. 2, 1993

Related U.S. Application Data

[63] Continuation-in-part of Ser. No. 756,994, Sep. 11, 1991, abandoned, which is a continuation-in-part of Ser. No. 498,561, Mar. 23, 1990, abandoned.

[30] Foreign Application Priority Data

Mar. 25, 1991 [EP] European Pat. Off. ............. 91200688

[51] Int. Cl.$^6$ ............... A01H 5/10; C12N 15/55; C12N 15/82; A23B 4/12
[52] U.S. Cl. ............. 800/250; 435/68.1; 435/69.1; 435/94; 435/95; 435/195; 435/200; 435/204; 435/209; 435/232; 435/233; 435/234; 426/7; 426/61; 426/531; 426/635
[58] Field of Search .................. 800/250, 205; 435/69.1, 240.5, 172.3, 68.1, 219, 94, 95, 195, 200, 204, 209, 234, 232, 233; 426/20, 21, 42, 44, 53, 54, 7, 61, 531, 615, 635

[56] References Cited

U.S. PATENT DOCUMENTS

| | | | |
|---|---|---|---|
| 19,210 | 1/1858 | Seitz | 435/93 |
| 109,991 | 12/1870 | Delamarre et al. | 435/93 |
| 579,739 | 3/1897 | Clowes et al. | 426/64 |
| 1,155,531 | 10/1915 | Walker | 426/53 |
| 2,219,368 | 10/1940 | McPherson et al. | 435/93 |
| 3,297,548 | 1/1967 | Ware et al. | 195/66 |
| 3,640,723 | 2/1972 | Uhlig et al. | 99/9 |
| 4,116,770 | 9/1978 | Goering et al. | 127/32 |
| 4,251,630 | 2/1981 | Pratt et al. | 435/98 |
| 4,458,017 | 7/1984 | Horwath et al. | 435/94 |
| 4,859,486 | 8/1989 | Douglass | 426/629 |
| 4,894,331 | 1/1990 | Ratzkin | 435/94 |
| 4,946,790 | 8/1990 | Fukuhara et al. | 435/252.33 |

FOREIGN PATENT DOCUMENTS

| | | | |
|---|---|---|---|
| 0380343 | 8/1980 | European Pat. Off. | A23J 1/14 |
| 0120516 | 10/1984 | European Pat. Off. | C12N 15/00 |
| 0159418 | 10/1985 | European Pat. Off. | C12N 15/00 |
| 0176112 | 4/1986 | European Pat. Off. | C12N 15/00 |
| 0179441 | 4/1986 | European Pat. Off. | A23L 1/03 |
| 0193259 | 9/1986 | European Pat. Off. | |
| 0224287 | 6/1987 | European Pat. Off. | C12N 15/00 |
| 0249432 | 12/1987 | European Pat. Off. | C12N 15/00 |
| 0255378 | 2/1988 | European Pat. Off. | C12N 15/00 |
| 0287152 | 10/1988 | European Pat. Off. | C12P 13/04 |
| 0318341 | 5/1989 | European Pat. Off. | C12N 15/00 |
| 0321004 | 6/1989 | European Pat. Off. | A23L 1/105 |
| 0346909 | 12/1989 | European Pat. Off. | A23K 3/00 |
| 0420358 | 4/1991 | European Pat. Off. | C12N 15/55 |
| 2505594 | 2/1974 | Germany | A23K 1/14 |
| 262041 | 11/1988 | Germany | C12N 15/00 |
| 275704 | 1/1990 | Germany | C12N 15/00 |
| WO87/00865 | 2/1987 | WIPO | |
| WO87/07299 | 12/1987 | WIPO | C12N 15/00 |
| WO89/03887 | 5/1989 | WIPO | C12P 21/02 |
| WO89/05859 | 6/1989 | WIPO | C12N 15/00 |
| WO89/12386 | 12/1989 | WIPO | A01H 1/04 |
| WO90/01551 | 2/1990 | WIPO | C12N 15/82 |
| WO90/02484 | 3/1990 | WIPO | A01H 5/00 |
| WO90/09436 | 8/1990 | WIPO | C12N 9/42 |
| 9010076 | 9/1990 | WIPO | |

OTHER PUBLICATIONS

L. Hoffman et al. Plant Mol. Biol., vol. 11 (1988) pp. 717–729.

T. Ohtani et al., Plant Mol. Biol., vol. 16 ('1991) pp. 117–128.

B. Larkins et al. J. Cell. Biochem., Suppl. O (9 Part C) p. 264 (1985).

C. Dorel et al. Plant Physiology, vol. '86 (4 Suppl.) (1988) p. 84.

R. Devlin, "Plant Physiology", 3rd Ed., N.Y., D. von Nostrand Co., 1975, p. 553.

R. Freedman et al. Cell, vol. 57, (Jun. 30, 1989) pp. 1069–1072.

R. Aebersold et al. PNAS, vol. 84 (Oct. 1987) pp. 6970–6974.

J. Sambrook et al., "Molecular Cloning, A Lab. Manual", CSHL Press, Cold Spring Harbor, NY, pp. 11.2–11.19, 11.45–11.49, & 11.52–11.61.

A. Kotovjansky et al. EMBO J., vol. 4, #3, ('1985) pp. 781–785.

G. Kawasaki et al. Biochem. Biophys. Res. Comm., vol. 108 (1982) pp. 1107–1112.

Altenbach et al., "Enhancement of the methionine content of seed proteins by the expression of a chimeric gene encoding a methionine–rich protein in transgenic plants" *Plant Mol. Biol.* (1989) 13(5):513–522.

Barker et al., "Cellular localization of soybean storage protein messenger RNA in transformed tobacco seeds" *Proc. Natl. Acad. Sci. USA* (1988) 85(2):458–462.

(List continued on next page.)

*Primary Examiner*—David T. Fox
*Assistant Examiner*—Charles Rories
*Attorney, Agent, or Firm*—Morrison & Foerster LLP

[57] ABSTRACT

A method of catalyzing in vitro reactions using seeds containing enhanced amounts of enzymes is disclosed. The method involves adding transgenic, non-wild type seeds, preferably in a ground form, to a reaction mixture and allowing the enzymes in the seeds to increase the rate of reaction. By directly adding the seeds to the reaction mixture the method provides a solution to the expensive and problematic process of extracting and purifying the enzyme. Methods of treatment are also provided whereby a subject lacking a sufficient supply of an enzyme is administered the enzyme in the form of seeds containing enhanced amounts of the enzyme.

15 Claims, 19 Drawing Sheets

OTHER PUBLICATIONS

Bustos et al., "Regulation of beta glucuronidase expression in transgenic tobacco plants by an adenosine thymidine–rich cis-acting sequence found upstream of a french bean beta phaseolin gene" *Plant Cell* (1989) 1(9):839–854.

Casey et al., "The structure of plant storage protein genes" *Plant Mol. Biol. Reporter* (1987) 5(2):261–281.

Christen et al., "Cloning of the phytase gene from germinating soybeans" *J. Cell Biochem.* (1988) Supplement 12, Part C, p. 190, (abstract No. L402).

Ellis et al., "Tissue–specific expression of a pea legumin gene in seeds of *Nicotiana plumbaginifolia*" *Plant Mol. Biol.* (1988) 10(3):203–214.

Gibson et al., "Phytase expression during seed germination" *J. Cell Biochem.* (1988) Supplemental 12, Part C, p. 192 (abstract No. L407).

Higgins et al., "The sequence of a pea vicilin gene and its expression in transgenic tobacco plants" *Plant Mol. Biol.* (1988) 11(5):683–696.

Hoffman et al., "Synthesis and protein body deposition of maize 15-kD zein in transgenic tobacco seeds" *EMBO J.* (1987) 6(11):3213–3222.

Krebbers et al., "Production of peptides in plant seeds" *Trends in Biotechnol.* (1990) 8(1):1–3.

Shotwell et al., In: *The Biochemistry of Plants*, vol. 15, Stumpf, P. K. & Conn, E. E., eds. (Academic Press, San Diego, 1989), chap. 7, pp. 297–345.

Sijmons et al., "Production of correctly processed human serum albumin in transgenic plants" *Biotechnology* (1990) 8(3):217–221.

Vandekerckhove et al., "Enkephalins produced in transgenic plants using modified 2S seed storage proteins" *Biotechnology* (1989) 7:929–932.

Derwent Publication "Alerting Abstracts Bulletin", Abstract No. 90–210631/28, which abstracts DDR application 23.09.88–DD–320082 (31 Jan. 1990).

Han et al., "Phytate hydrolysis in soybean and cottonseed meals by *Aspergillus ficuum* phytase" *J. Agric. Food Chem.* (1988) 36(2):259–262.

Han, Y. W., "Removal of phytic acid form soybean and cottonseed meals" *J. Agric. Food Chem.* (1988) 36(6):1181–1183.

*Patent Abstracts of Japan* vol. 9, No. 17, (C–262) [1740] Jan. 24, 1985.

Jordano et al., "A sunflower helianthinin gene upstream sequence ensemble contains an enhancer and sites of nuclear protein interaction" *Plant Cell* (1989) 1(9):855–866.

Hesselman et al., "The effect of β–glucanase on the utilization of starch and nitrogen by broiler chickens fed on barley of low–or–high–viscosity" *Chem. Abstracts.* (1986) 105:574 (abstract No. 132749x).

Broz et al., "Effects of β–glucanase on the feeding value of broiler diets bsed on barley or oats" *Chem. Abstracts* (1986) 105:569 (abstract No. 23478n).

Gopaldas et al., "Studies on wheat–based amylase–rich food" *Food Science Technol. Abstracts* (1989) 21(8):123 (abstract No. 8 M 19).

Goldberg et al., "Regulation of gene expression during plant embryogenesis" *Cell* (1989) 56:149–160.

Dorel et al., "Transport of proteins to the plant vacuole is not by bulk flow through the secretory system, and requires positive sorting information" *J. Cell Biol.* (1989) 108:327–337.

Voelker et al., "In vitro mutated phytohemagglutinin genes expressed in tobacco seeds: role of glycans in protein targeting and stability" *Plant Cell* (1989) 1:95–104.

Della–Chioppa et al., "Protein tracking in plant cells" *Plant Physiol.* (1987) 84:965–968.

Perlman et al., "A putative signal peptidase recognition site and sequence in eukaryotic and prokaryotic signal peptides" *J. Mol. Biol.* (1983) 167:391–409.

von Heline, G., "How signal sequences maintain cleavage specificity" *J. Mol. Biol.* (1984) 173:243–251.

Schmülling et al., "Single genes from *Agrobacterium rhizogenes* influence plant development" *EMBO J.* (1988) 7(9):2621–2629.

Palmiter et al., "cell lineage ablation in transgenic mice by cell–specific expression of a toxin gene" *Cell* (1987) 50:435–443.

Williams et al., "Embryonic lethalities and endothelial tumors in chimeric mice expression polyoma virus middle T oncogene" *Cell* (1988) 52:121–131.

Dunphy et al., "Unraveling of mitotic control mechanisms" *Cell* (1988) 55:925–928.

Soloman et al., "Cyclin in fission yeast" *Cell* (1988) 54:738–740.

Jähne et al., "Regeneration of fertile plants from protoplasts derived from embryogenic cell suspensions of barley" (*Hordeum vulgare* L.) *Plant Cell Reports* (1991) 10:1–6.

Brown et al., "Developmental regulation of mutator activity in maize" *J. Cell. Biochem.* (1988) Supplement 12C:190.

Christen et al., "Cloning of the phytase gene from germinating soybeans" *J. Cell. Biochem.* (1988) Supplement 12C:190.

Chu et al.,, "Stage–specific expression in the shoot apex during early floral development" *J. Cell. Biochem.* (1988) Supplement 12C:190.

Ullah et al., "Extracellular phytase (E.C.3.1.3.8) from *Aspergillus ficuum* NRRL 3135: purification and characterization" *Prep. Biochem.* (1987) 17(1):63–91.

Matsuda et al. "The primary structure of L–1 light chain of chicken fast skeletal muscle myosin and its genetic implication" *FEBS Letters* (1981) 126(1):111–113.

Jaye et al., "Isolation of human anti–haemophilic factor IX cDNA clone using a unique 52–Base synthetic oligonucleotide probe derived from the amino acid sequence of bovine factor IX" *Nucl. Acids Res.* (1983) 11(8):2325–2335.

Ortlepp et al., "Molecular cloning in a *Bacillus licheniformis* gene encoding a thermostable alpha–amylase" *Gene* (1983) 23:267–276.

Cornellissen et al., "A tobacco mosaic virus–induced tobacco protein is homologous to the sweet–tasting protein thaumatin" *Nature* (1986) 321:531–532.

Ryan et al., "Genomic sequence of a 12S seed storage protein from oilseed rape (*Brassica napus* c.v. jet neuf)" *Nucl. Acids Res.* (1989) 17(9):3584.

Luerssen et al., "The nucleotide sequence of rat transition protein 2 (TP2) cDNA" *Nucl. Acids Res.* (1989) 17(9):3585.

Iturriaga et al., "Endoplasmic reticulum targeting and glycosylation of hybrid proteins in transgenic tobacco" *Plant Cell* (1989) 1:381–390.

Jobling et al., "Enhanced translation of chimaeric messenger RNAs containing a plant viral untranslated leader sequence" *Nature* (1987) 325:622–625.

Kay et al., "Duplication of CaMV 35S promoter sequences creates a strong enhancer for plant genes" *Science* (1987) 236:1299–1302.

Baulcombe et al., "Expression of biologically active viral satellite RNA from the nuclear genome of transformed plants" *Nature* (1986) 321:446–449.

Brooks, A. D., "Molecular cloning of the structural gene for exopolygalacturonate lyase from *Erwina chysanthemi* EC16 and characterization of the enzyme product" *J. Bacteriol.* (1990 172:6950–6958.

Chrispeels, M. J., "Sorting of proteins in the secretory system" *Ann. Rev. Plant Physiol. Plant Mol. Biol.* (1991) 42:1–24.

Fischoff et al., "Insect tolerant transgenic tomato plants" *Biotechnology* (1987) 5:807–813.

Perlak et al., "Modification of the coding sequence enhances plant expression of insect control protein genes" *Proc. Natl. Acad. Sci.* (1991) 88:3324–3328.

Vaeck et al., "Transgenic plants protected from insect attack" *Nature* (1987) 328:33–37.

John et al., "Reduction in the dietary bulk of soya–fortified bulgur wheat gruels with wheat–based amylase–rich food" *Food Science Technol. Abstracts* (1989) 21(12):124 (abstract No. 12 M 11).

```
                                                                         EcoRI
TATTTACGTT  CGGTCGGATA  ACGGACGGGT  TTTCAGTTCG  GGTTCGGTTC  GGATTTCGGG
TTCCGGATTT  ATATGGCCCT  AGCCTAAATT  CGAGTGTGAC  CGTTAATCCG  TTATACTACG
ATCTAATCAA  AACATGTCTA  GATCAAATTT  GCAATCTTAT  TGCATATTTT  TTTGTCTAAC
AATATTACTA  GAAATCTTTG  TTTATTACCA  ACATTAGTAA  AACTATATCT  TAACCAAAGT
TGCAGGAGCA  GTTCGTTTCA  AACGTAATTG  CTATAGTGAT  GTTATTGTAA  ATTTGTTATA
CTGATCAAAT  GTAAAGAATA  ATACAATTTT  GACAAACAAA  TCAGTATATA
TATACAAGAA  ATATATATTT  TGTCCTATTA  CATATGCCTA  TCTCAAAGTT  GATGTGTAAA
GACATGCAGT  TCAATAAGCC  ATGCAAATTG  AGATGTGTCA  AACTCCCTTC  GTTAATATGT
GTTTTCTTAC  AATGTGAAGC  CAAATTAAAT  TTTCAGAAGA  AGACATAAAG  ATAGCAACTC
AAATGAAGTG  TAGATTGTAC  ATAGTCGACT  CTATATACCT  GGTTCTTATC  TCATTCAATT
TATCCTCAAA  AAAATTTATC  AACATCTATA  CAAATAAGTT  CACTATAAAT  AGCTTCATCT
                                                      *
AACTCAGCTG  TAAGACCAGA  AAAACCACAA  CAACTAAGTA  AAGAGAAAAT  GGCTCGGCTC
                                                    NcoI
TCATCTCTTC  TCTCTTTTTC  CTTAGCACTT  TTGACTTTTC  TCCATGGCTC  TACAGCTCAA
CAGTTTCCAA  ACGAGTGTCA  GCTAGACCAG  CTCAATGCAC  TGGAGCCGTC  ACACGTACTT
AAGGCTGAGG  CTGGTCGCAT  CGAGGTGTGG  GACCACCACG  CTCCTCAGCT  ACGTTGCTCT
GGTGTCTCCT  TTGTACGTTA  CATCATCGAG  TCTAAGGGTC  TCTACTTGCC  CTCTTTCTTT
AGCACCGCGA  GGCTCTCCTT  CGTGGCTAAA  GGTACGTGAA  TCTGATTTTG  ATACTATATG
```

FIG.3A

```
AGTATCGAGA TTCAAATTCG TGATCTTTAA GGTTCAGTCT TTTGAGAAAA GTGTTGTAGT
AAGTATATCA CTATACACGT GCTAAGGTTT TGATCAAATA CATTATAATA TTTTTTTGTT
TAATTATAA CCTAAATATA TGGTCGATGT TCACAGAACT GCGCACTAAA TTTTTTTTT
TTGGTTTGTT ACATTATAGG AGAAGGTCTT ATGGGGAGAG TGGTCCTGTG CGCCGAGACA
TTCCAGGACT CATCAGTGTT TCAACCAAGC GGTGGTAGCC CCTTCGGAGA AGGTCAGGGC
CAAGGACAAC AAGGTCAGGG CCAAGGCCAC CAAGGTCAAG GCCAAGGACA ACAGGGCCAA
CAAGGTCAGC AAGGACAACA GAGTCAAGGC CAGGGTTTCC GTGATATGCA CCAGAAAGTG
GAGCACATAA GGACTGGGGA CACCATCGCT ACACATCCCG GTGTAGCCCA ATGGTTCTAC
AACGACGGAA ACCAACCACT TGTCATCGTT TCCGTCCTCG ATTTAGCCAG CCACCAGAAT
CAGCTCGACC GCAACCCAAG GGTATATAAA TAAACAAAAA CCTCAAAAGC AATCAAGGGC
AAATCTCCTT TTTAGCATAT TTCTAAATTT ATATCACAAA TTTTAATTTT TTTATTTTTC
ATGACCAAAA TCATACTTTT CTAAGTTTAT CCTTTGAAAA TCTCAACCCT AAACCATAAC CCTAATCTAA
AAATTTGAAT CTATAGCGCC AAACCTCATT TCTCAACCCT AAATCCTAAA CCCCAGCCTT
ACCTTAAACC CTAAACCCCA AACCCTAAAC CCTAAAACCCT AAACATTAAG TGCTATTTTG
AAACTCTAAA CCCTAAAACCC TAAGTTTGTG ACTTTTGATA AAACATTAAG TTTTTGTCTT
TGACTTTGAC CTTGGTGCTA GTTTGAGAAC ATAAACTTGA TTTAGTGCTA TTTCTGTTTT
TTTCTCATCA TATAACTTCT TTTATAATTA CAGAATATCA AAAATATGGT ATAGAAGGAC
ATCTGTAGCC ATTTTACTTA GCCGAAACA ACCCACAAGG CCAAGTATGG CTTGCTAAAG
GCGAGCAACA GCCACAAAAG AACATCCTTA ATGGCTTCAC ACCAGAGGTT AACCGTGGAA
CTTTCAAGAT CGATGTTAGG ACAGGCCAAC AACTTCAGAA CCAGCAAGAC AGTCAGAGAC
ACATTATCCG AGTCCAAGGC CCATTCAGTG TCATTAGGCC GCCTTTGAGG ACCGATAACC
CGCAGGAGGA AGTTAACGGT TTAGAAGAGA CCATATGCAG CGCGAGGTGC
```

FIG.3B

```
TCGATGACCC ATCTAATGCT GACGTATACA AGCCACAGCT CGGTTACATC AGCACTCTGA
ACAGCTATGA TCTCCCCATC CTTCGCTTCC TTCGTCTCTC AGCCCTCCGT GGATCTATCC
GTCAAAACGC GATGGTGCTT CCACAGTGGA ACGCAAACGC AAACGGCGGTT CTCTACGTGA
CAGACGGGGA AGCCCATGTG CAGGTGGTTA ACGACAACGG TGACAGAGTG TTCGACGGAC
AAGTCTCTCA AGGACAGCTA CTTTCCATAC CACAAGGTTT CTCCGTGGTG AAACGCGCAA
CAAGCGAACA GTTCCGGTGG ATCGAGTTCA AGACAAAACGC AAACGCACAG ATCAACACAC
TTGCTGGACG AACCCTCGGTC TTGAGAGGTT TACCATTAGA GGTCATATCC AATGGGTACC
AAATCTCACT CGAAGAAGCA AGAAGGGTTA AGTTCAACAC GATCGAGACC ACTTTGACGC
                                                        BglII
ACAGCAGTGG CCCAGCTAGC TACGGAGGGC CAAGGAAGGC TGATGCTTAA GAGCTTACCC
AGTGAACCTC TACTGTAAAA GGAAGTTAAA TAGTAATAAA AAGAGTAATA ATAATGTACG
CAAATGTGAC TGGTTTTGTA GAGGTTTTAG AATGTTACTC CTTTTCTGAA TAAAATAACT
CTTTTCTATC AAGGTTTAGC TAGCTGGGCT AATCTATCAA CTTCATTTTT CGACTACGTC
                HindIII
TACACATACG TATACGAGAT GCAGGCTTCT CCGAGGATAT AGTGACAGTA TCT
```

FIG.3C

Oligonucleotide duplex A

```
                                      NcoI       BamHI  HindIII
5'GGGTTTTTATTTTAATTTCTTTCAAATACTTCCACCATGGGTAACGGATCCA     3'
3'CCCAAAAATAAAATTAAAGAAAGTTTATGAAGGTGGTACCCATTGCCTAGGTTCGA 5'
```

Oligonucleotide duplex B

```
5'CATGAACTTCCTCAAGAGAGCTTCCCCTTTATGCCTTCCTTGTTTTTGGCCAATACTTTGTAGCTGTTACGCATGCTCGAG 3'
3'    TGAAGGAGTTCTCGAAGGGGAAATACGGAAGGAAACAAAACCGGTTATGAAACATCGACAATGCGTACGAGCTCCTAG 5'
                                                                 SphI  XhoI  BamHI
```

Oligonucleotide duplex C

```
     SphI                XhoI      PstI BamHI
5'      CT|CTGGCAGTCCCCGCCTCGAGCCCCCTGCAG    3'
3' GTACGA|GACCGTCAGGGGCGGAGCTCGGGGGACGTCCTAG 5'
       PROB12 Mature phytase
       signal
       peptide
```

FIG.4A oligonucleotide duplex D

```
         NcoI                                              XhoI EcoRV PstI       BglII          HindIII
                 HisGlySerThrAla|LeuAlaValProAlaSer
         5' CATGGCTCTACAGCT     CTGGCAGTCCCCGCCCTCGAGGATATCCTGCAGATCTCCCCA 3'
         3'      CGAGATGTCGA    GACCGTCAGGGGCGGGAGCTCCTATAGGACGTCTAGAGGGGGTTCGA 5'
                 CruA signal    Mature phytase     Multiple cloning site
                 peptide
``` oligonucleotide duplex E

```
         5' AATTCAGATCTCCATGGATCGATGAGCT 3'
         3'     GTCTAGAGGTACCTAGCTAC     5'
``` oligonucleotide duplex F

```
         SphI                         HgaI SITE
                                      α-AMYLASE
              CT GCAAATCTTAATGGACGCTGATG         3'
         5'
         3' GTACGA CGTTTAGAATTACCCTGCGACTACGTCAT 5'
              PROB12  α-Amylase
              signal
              peptide
```

FIG.4B

```
Xbal
      *
TCTAGAGTC  ATGAAACAAC  AAAAACGGCT  TTACGCCCGA  TTGCTGACGC  TGTTATTTGC
                         PstI                                HgaI
GCTCATCTTC TTGCTGCCTC   ATTCTGCAGC AGCGGGCGGCA AATCTTAATG GGACGCTGAT
GCAGTATTTT GAATGGTACA   TGCCCAATGA CGGCCAACAT  TGGAAGCGTT TGCAAAACGA
CTCGGCATAT TTGGCTGAAC   ACGGTATTAC TGCCGTCTGG  ATTCCCCCGG  CATATAAGGG
AACGAGCCAA GCGGATGTGG   GCTACGGTGC TTACGACCTT  TATGATTTAG  GGGAGTTTCA
TCAAAAAGGG ACGGTTCGGA   CAAAGTACGG CACAAAAGGA  GAGCTGCAAT  CTGCGATCAA
AAGTCTTCAT TCCCGCGACA   TTAACGTTTA CGGGGATGTG  GTCATCAACC  ACAAAGGCGG
CGCTGATGCG ACCGAAGATG   TAACCGCGGT TGAAGTCGAT  CCCGCTGACC  GCAACCGCGT
AATTTCAGGA GAACACCTAA   TTAAAGCCTG GACACATTTT  CATTTTCCGG  GGCGCGGCAG
CACATACAGC GATTTTAAAT   GGCATTGGTA CCATTTTGAC  GGAACCGATT  GGGACGAGTC
CCGAAAGCTG AACCGCATCT   ATAAGTTTCA AGGAAAGGCT  TGGGATTGGG  AAGTTTCCAA
TGAAAACGGC AACTATGATT   ATTTGATGTA TGCCGACATC  GATTATGACC  ATCCTGATGT
CGCAGCAGAA ATTAAGAGAT   GGGCACTTG  GTATGCCAAT  GAACTGCAAT  TGGACGGTTT
CCGTCTTGAT GCTGTCAAAC   ACATTAAATT TTCTTTTTTG  CGGGATTGGG  TTAATCATGT
CAGGGAAAAA ACGGGGAAGG   AAATGTTTAC GGTAGCTGAA  TATTGGCAGA  ATGACTTGGG
```

FIG.7A

```
CGGGCTGGAA AACTATTTGA ACAAAACAAA TTTTAATCAT TCAGTGTTTG ACGTGCCGCT
TCATTATCAG TTCCATGCTG CATCGACACA GGGAGGCCGG TATGATATGA GGAAATTGCT
GAACGGTACG GTCGTTTCCA AGCATCCGTT GAAATCGGTT ACATTTGTCG ATAACCATGA
TACACAGCCG GGGCAATCGC TTGAGTCGAC TGTCCAAACA TGGTTTAAGC CGCTTGCTTA
                                Sal I
CGCTTTTATT CTCACAAGGG AATCTGGATA CCCTCAGGTT TTCTACGGGG ATATGTACGG
GACGAAAGGA GACTCCCAGC GCGAAATTCC TGCCTTGAAA CACAAAATTG AACCGATCTT
AAAAGCGAGA AAACAGTATG CGTACGGAGC ACAGCATGAT TATTTCGACC ACCATGACAT
TGTCGGCTGG ACAAGGGAAG GCGACAGCTC GGTTGCAAAT TCAGGTTTGG CGGCATTAAT
AACAGACGGA CCCGGTGGGG CAAAGGGAAT GTATGTCGGC GCCGGTTGTC CGGCAAAACG CCGGTGAGAC
ATGGCATGAC ATTACCGGAA ACCGTTCGGA GCCGGTTGTC ATCAATTCGG AAGGCTGGGG
AGAGTTTCAC GTAAACGGCG GGTCGGTTTC AATTTATGTT CAAAGATAGA AGAGCAGAGA
GGACGGATTT CCTGAAGGAA ATCCGTTTTT TTATTTTGCC CGTCTTATAA ATTTCTTTGA
 BamHI
TTACATTTTA TAATTAATTT TAACAAAGTG TCATCAGCCC TCAGGAAGGA CTTGCTGACA
GTTTGAATCG CATAGGTAAG GCGGGGATGA AATGGCAACG TTATCTGATG TAGCAAAGAA
AGCAAATGTG TCGAAAATGA CGGTATCGCG GGTGATCA
                                 BclI
```

FIG.7B

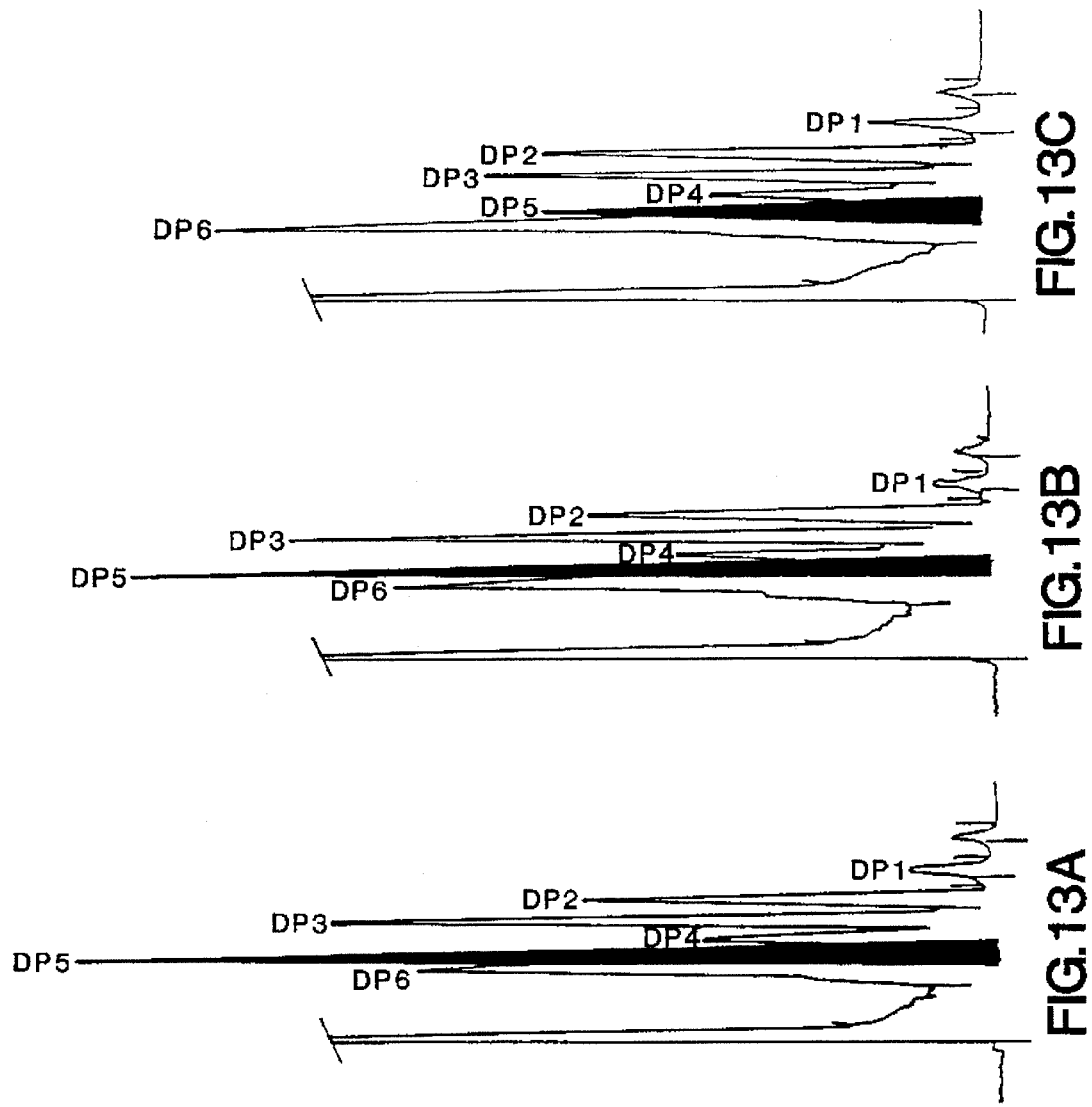

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GGGTAGAATT  CAAAAATGGG  CGTCTCTGCT  GTTCTA                              36
```

( 2 ) INFORMATION FOR SEQ ID NO:2:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
AGTGACGAAT  TCGTGCTGGT  GGAGATGGTG  TCG                                 33
```

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
GAGCACCAAG  CTGAAGGATC  C                                               21
```

( 2 ) INFORMATION FOR SEQ ID NO:4:

( i ) SEQUENCE CHARACTERISTICS:
        ( A ) LENGTH: 34 base pairs
        ( B ) TYPE: nucleic acid

```
              ( C ) STRANDEDNESS: single
              ( D ) TOPOLOGY: linear ( x i ) SEQUENCE DESCRIPTION: SEQ ID NO:4:

AAACTGCAGG CGTTGAGTGT GATTGTTTAA AGGG                                          3 4

( 2 ) INFORMATION FOR SEQ ID NO:5:

( i ) SEQUENCE CHARACTERISTICS:
              ( A ) LENGTH: 20 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:5:

GTTCGGAATT CGGGTTCCGG                                                          2 0

( 2 ) INFORMATION FOR SEQ ID NO:6:

( i ) SEQUENCE CHARACTERISTICS:
              ( A ) LENGTH: 20 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:6:

AACTGTTGAG CTGTAGAGCC                                                          2 0

( 2 ) INFORMATION FOR SEQ ID NO:7:

( i ) SEQUENCE CHARACTERISTICS:
              ( A ) LENGTH: 20 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:7:

CTTAAGATCT TACCCAGTGA                                                          2 0

( 2 ) INFORMATION FOR SEQ ID NO:8:

( i ) SEQUENCE CHARACTERISTICS:
              ( A ) LENGTH: 20 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:8:

CGGAGAAGCT TGCATCTCGT                                                          2 0

( 2 ) INFORMATION FOR SEQ ID NO:9:

( i ) SEQUENCE CHARACTERISTICS:
              ( A ) LENGTH: 20 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:9:

AGCTCTGCAG TGAGGTACCA                                                          2 0

( 2 ) INFORMATION FOR SEQ ID NO:10:

( i ) SEQUENCE CHARACTERISTICS:
              ( A ) LENGTH: 20 base pairs
              ( B ) TYPE: nucleic acid
              ( C ) STRANDEDNESS: single
              ( D ) TOPOLOGY: linear
```

( x i ) SEQUENCE DESCRIPTION: SEQ ID NO:10:

AGCTTGGTAC CTCACTGCAG 20

( 2 ) INFORMATION FOR SEQ ID NO:11:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

CGCGAATTCT GCAGCCAGAA GGATAAAG 28

( 2 ) INFORMATION FOR SEQ ID NO:12:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GTGGTCGCCA TGGTCGATAT TCACG 25

( 2 ) INFORMATION FOR SEQ ID NO:13:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

CATGAACTTC CTCAAGAGCT TCCCTTTTA TGCCTTCCTT TGTTTTG 47

( 2 ) INFORMATION FOR SEQ ID NO:14:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

AAAACAAAGG AAGGCATAAA AGGGGAAGCT CTTGAGGAAG TT 42

( 2 ) INFORMATION FOR SEQ ID NO:15:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

GCCAATACTT TGTAGCTGTT ACGCATGCTC GAG 33

( 2 ) INFORMATION FOR SEQ ID NO:16:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

GATCCTCGAG CATGCGTAAC AGCTACAAAG TATTGGCC                              38

( 2 ) INFORMATION FOR SEQ ID NO:17:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

CAGAGCATGC GTAACAGCTA C                                                21

( 2 ) INFORMATION FOR SEQ ID NO:18:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

CGGAATTCGG CAGCTGTAAG ACCAGAGGGT TTTTATTTTT A                          41

( 2 ) INFORMATION FOR SEQ ID NO:19:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

GGAATTCTGG TACCTCCCGG GAGGATCCAT CTAGAGCTCG AGTAAGCTTC                 50

( 2 ) INFORMATION FOR SEQ ID NO:20:

( i ) SEQUENCE CHARACTERISTICS:
        ( A ) LENGTH: 3113 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

TATTTACGTT CGGTCGGATA ACGGACGGGT TTTCAGTTCG GGTTCGGTTC GGATTTCGGG      60

TTCCGGATTT ATATGGCCCT AGCCTAAATT CGAGTGTGAC CGTTAATCCG TTATACTACG     120

ATCTAATCAA AACATGTCTA GATCAAATTT GCAATCTTAT TGCATATTTT TTTGTCTAAC     180

AATATTACTA GAAATCTTTG TTTATTACCA ACATTAGTAA AACTATATCT TAACCAAAGT     240

TGCAGGAGCA GTTCGTTTCA AACGTAATTG CTATAGTGAT GTTATTGTAA ATTTGTTATA     300

CTGATCAAAT GTAAAGAATA ATACAATTTT ATATATATCT GACAAACAAA TCAGTATATA     360

TATACAAGAA ATATATATTT TGTCCTATTA CATATGCCTA TCTCAAAGTT GATGTGTAAA     420

GACATGCAGT TCAATAAGCC ATGCAAATTG AGATGTGTCA AACTCCCTTC GTTAATATGT     480

GTTTTCTTAC AATGTGAAGC CAAATTAAAT TTCAGAAGA AGACATAAAG ATAGCAACTC      540

AAATGAAGTG TAGATTGTAC ATAGTCGACT CTATATACCT GGTTCTTATC TCATTCAATT     600

TATCCTCAAA AAAATTTATC AACATCTATA CAAATAAGTT CACTATAAAT AGCTTCATCT     660

AACTCAGCTG TAAGACCAGA AAAACCACAA CAACTAAGTA AAGAGAAAAT GGCTCGGCTC     720

TCATCTCTTC TCTCTTTTTC CTTAGCACTT TTGACTTTTC TCCATGGCTC TACAGCTCAA     780

CAGTTTCCAA ACGAGTGTCA GCTAGACCAG CTCAATGCAC TGGAGCCGTC ACACGTACTT     840

```
AAGGCTGAGG  CTGGTCGCAT  CGAGGTGTGG  GACCACCACG  CTCCTCAGCT  ACGTTGCTCT    900
GGTGTCTCCT  TTGTACGTTA  CATCATCGAG  TCTAAGGGTC  TCTACTTGCC  CTCTTTCTTT    960
AGCACCGCGA  GGCTCTCCTT  CGTGGCTAAA  GGTACGTGAA  TCTGATTTTG  ATACTATATG   1020
AGTATCGAGA  TTCAAATTCG  TGATCTTTAA  GGTTCAGTCT  TTTGAGAAAA  GTGTTGTAGT   1080
AAGTATATCA  CTATACACGT  GCTAAGGTTT  TGATCAAATA  CATTATAATA  TTTTTTTGTT   1140
TAATTTATAA  CCTAAATATA  TGGTCGATGT  TCACAGAACT  GCGCACTAAA  TTTTTTTTTT   1200
TTGGTTTGTT  ACATTATAGG  AGAAGGTCTT  ATGGGGAGAG  TGGTCCTGTG  CGCCGAGACA   1260
TTCCAGGACT  CATCAGTGTT  TCAACCAAGC  GGTGGTAGCC  CCTTCGGAGA  AGGTCAGGGC   1320
CAAGGACAAC  AAGGTCAGGG  CCAAGGCCAC  CAAGGTCAAG  GCCAAGGACA  ACAGGGCCAA   1380
CAAGGTCAGC  AAGGACAACA  GAGTCAAGGC  CAGGGTTTCC  GTGATATGCA  CCAGAAAGTG   1440
GAGCACATAA  GGACTGGGGA  CACCATCGCT  ACACATCCCG  GTGTAGCCCA  ATGGTTCTAC   1500
AACGACGGAA  ACCAACCACT  TGTCATCGTT  TCCGTCCTCG  ATTTAGCCAG  CCACCAGAAT   1560
CAGCTCGACC  GCAACCCAAG  GGTATATAAA  TAAACAAAAA  CCTCAAAAGC  AATCAAGGGC   1620
AAATCTCCTT  TTTAGCATAT  TTCTAAATTT  ATATCACAAA  AATAGCAATC  AAAAACTAAA   1680
ATGACCAAAA  TCATACTTTT  CTAAGTTTAT  CCTTTGAAAA  TTTTAATTTT  TTTATTTTTC   1740
AAATTTGAAT  CTATACGCCC  AAACCTCATT  TCTCAACCCT  AAACCATAAC  CCTAATCTAA   1800
ACCTTAAACC  CTAAACCCCA  AACCCTAAAC  CCTAAACCCT  AAATCCTAAA  CCCCAGCCTT   1860
AAACTCTAAA  CCCTAAACCC  TAAGTTTGTG  ACTTTGATA   AAACATTAAG  TGCTATTTTG   1920
TGACTTTGAC  CTTGGTGCTA  GTTTGAGAAC  ATAAACTTGA  TTTAGTGCTA  TTTTTGTCTT   1980
TTTCTCATCA  TATAACTTCT  TTTATAATTA  CAGAATATCA  AAAATATGGT  TTTCTGTTTT   2040
ATCTGTAGCC  ATTTTACTTA  GCCGGAAACA  ACCCACAAGG  CCAAGTATGG  ATAGAAGGAC   2100
GCGAGCAACA  GCCACAAAAG  AACATCCTTA  ATGGCTTCAC  ACCAGAGGTT  CTTGCTAAAG   2160
CTTTCAAGAT  CGATGTTAGG  ACAGCGCAAC  AACTTCAGAA  CCAGCAAGAC  AACCGTGGAA   2220
ACATTATCCG  AGTCCAAGGC  CCATTCAGTG  TCATTAGGCC  GCCTTTGAGG  AGTCAGAGAC   2280
CGCAGGAGGA  AGTTAACGGT  TTAGAAGAGA  CCATATGCAG  CGCGAGGTGC  ACCGATAACC   2340
TCGATGACCC  ATCTAATGCT  GACGTATACA  AGCCACAGCT  CGGTTACATC  AGCACTCTGA   2400
ACAGCTATGA  TCTCCCCATC  CTTCGCTTCC  TTCGTCTCTC  AGCCCTCCGT  GGATCTATCC   2460
GTCAAAACGC  GATGGTGCTT  CCACAGTGGA  ACGCAAACGC  AAACGCGGTT  CTCTACGTGA   2520
CAGACGGGGA  AGCCCATGTG  CAGGTGGTTA  ACGACAACGG  TGACAGAGTG  TTCGACGGAC   2580
AAGTCTCTCA  AGGACAGCTA  CTTTCCATAC  CACAAGGTTT  CTCCGTGGTG  AAACGCGCAA   2640
CAAGCGAACA  GTTCCGGTGG  ATCGAGTTCA  AGACAAACGC  AAACGCACAG  ATCAACACAC   2700
TTGCTGGACG  AACCTCGGTC  TTGAGAGGTT  TACCATTAGA  GGTCATATCC  AATGGGTACC   2760
AAATCTCACT  CGAAGAAGCA  AGAAGGGTTA  AGTTCAACAC  GATCGAGACC  ACTTTGACGC   2820
ACAGCAGTGG  CCCAGCTAGC  TACGGAGGGC  CAAGGAAGGC  TGATGCTTAA  GAGCTTACCC   2880
AGTGAACCTC  TACTGTAAAA  GGAAGTTAAA  TAGTAATAAA  AAGAGTAATA  ATAATGTACG   2940
CAAATGTGAC  TGGTTTTGTA  GAGGTTTTAG  AATGTTACTC  CTTTTCTGAA  TAAAATAACT   3000
CTTTTCTATC  AAGGTTTAGC  TAGCTGGGCT  AATCTATCAA  CTTCATTTTT  CGACTACGTC   3060
TACACATACG  TATACGAGAT  GCAGGCTTCT  CCGAGGATAT  AGTGACAGTA  TCT          3113
```

( 2 ) INFORMATION FOR SEQ ID NO:21:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:21:

GGGTTTTTAT TTTTAATTTT CTTTCAAATA CTTCCACCAT GGGTAACGGA TCCA      54

( 2 ) INFORMATION FOR SEQ ID NO:22:

( i ) SEQUENCE CHARACTERISTICS:
    ( A ) LENGTH: 58 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:22:

AGCTTGGATC CGTTACCCAT GGTGGAAGTA TTTGAAAGAA AATTAAAAAT AAAAACCC      58

( 2 ) INFORMATION FOR SEQ ID NO:23:

( i ) SEQUENCE CHARACTERISTICS:
    ( A ) LENGTH: 80 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:23:

CATGAACTTC CTCAAGAGCT TCCCCTTTTA TGCCTTCCTT TGTTTTGGCC AATACTTTGT      60

AGCTGTTACG CATGCTCGAG      80

( 2 ) INFORMATION FOR SEQ ID NO:24:

( i ) SEQUENCE CHARACTERISTICS:
    ( A ) LENGTH: 79 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:24:

GATCCTCGAG CATGCGTAAC AGCTACAAAG TATTGGCCAA AACAAAGGAA GGCATAAAAG      60

GGGAAGCTCT TGAGGAAGT      79

( 2 ) INFORMATION FOR SEQ ID NO:25:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:25:

CTCTGGCAGT CCCCGCCTCG AGCCCCCTGC AG      32

( 2 ) INFORMATION FOR SEQ ID NO:26:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:26:

GATCCTGCAG GGGCTCGAG GCGGGGACTG CCAGAGCATG      40

( 2 ) INFORMATION FOR SEQ ID NO:27:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

CATGGCTCTA CAGCTCTGGC AGTCCCCGCC TCGAGGATAT CCTGCAGATC TCCCCA     56

( 2 ) INFORMATION FOR SEQ ID NO:28:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

AGCTTGGGGA GATCTGCAGG ATATCCTCGA GGCGGGGACT GCCAGAGCTG TAGAGC     56

( 2 ) INFORMATION FOR SEQ ID NO:29:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

AATTCAGATC TCCATGGATC GATGAGCT     28

( 2 ) INFORMATION FOR SEQ ID NO:30:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

CATCGATCCA TGGAGATCTG     20

( 2 ) INFORMATION FOR SEQ ID NO:31:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

CTGCAAATCT TAATGGGACG CTGATG     26

( 2 ) INFORMATION FOR SEQ ID NO:32:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

TACTGCATCA GCGTCCCATT AAGATTTGCA GCATG     35

( 2 ) INFORMATION FOR SEQ ID NO:33:

(i) SEQUENCE CHARACTERISTICS:
    (A) LENGTH: 1777 base pairs
    (B) TYPE: nucleic acid
    (C) STRANDEDNESS: single
    (D) TOPOLOGY: linear (xi) SEQUENCE DESCRIPTION: SEQ ID NO:33:

```
TCTAGAGTCA  TGAAACAACA  AAAACGGCTT  TACGCCCGAT  TGCTGACGCT  GTTATTTGCG    60
CTCATCTTCT  TGCTGCCTCA  TTCTGCAGCA  GCGGCGGCAA  ATCTTAATGG  GACGCTGATG   120
CAGTATTTTG  AATGGTACAT  GCCCAATGAC  GGCCAACATT  GGAAGCGTTT  GCAAACGAC    180
TCGGCATATT  TGGCTGAACA  CGGTATTACT  GCCGTCTGGA  TTCCCCCGGC  ATATAAGGGA   240
ACGAGCCAAG  CGGATGTGGG  CTACGGTGCT  TACGACCTTT  ATGATTTAGG  GGAGTTTCAT   300
CAAAAAGGGA  CGGTTCGGAC  AAAGTACGGC  ACAAAGGAG   AGCTGCAATC  TGCGATCAAA   360
AGTCTTCATT  CCCGCGACAT  TAACGTTTAC  GGGGATGTGG  TCATCAACCA  CAAGGCGGC    420
GCTGATGCGA  CCGAAGATGT  AACCGCGGTT  GAAGTCGATC  CCGCTGACCG  CAACCGCGTA   480
ATTTCAGGAG  AACACCTAAT  TAAAGCCTGG  ACACATTTTC  ATTTTCCGGG  GCGCGGCAGC   540
ACATACAGCG  ATTTTAAATG  GCATTGGTAC  CATTTGACG   GAACCGATTG  GGACGAGTCC   600
CGAAAGCTGA  ACCGCATCTA  TAAGTTTCAA  GGAAAGGCTT  GGGATTGGGA  AGTTTCCAAT   660
GAAAACGGCA  ACTATGATTA  TTTGATGTAT  GCCGACATCG  ATTATGACCA  TCCTGATGTC   720
GCAGCAGAAA  TTAAGAGATG  GGGCACTTGG  TATGCCAATG  AACTGCAATT  GGACGGTTTC   780
CGTCTTGATG  CTGTCAAACA  CATTAAATTT  TCTTTTTTGC  GGGATTGGGT  TAATCATGTC   840
AGGGAAAAAA  CGGGGAAGGA  AATGTTTACG  GTAGCTGAAT  ATTGGCAGAA  TGACTTGGGC   900
GCGCTGGAAA  ACTATTTGAA  CAAAACAAAT  TTTAATCATT  CAGTGTTTGA  CGTGCCGCTT   960
CATTATCAGT  TCCATGCTGC  ATCGACACAG  GGAGGCGGCT  ATGATATGAG  GAAATTGCTG  1020
AACGGTACGG  TCGTTTCCAA  GCATCCGTTG  AAATCGGTTA  CATTTGTCGA  TAACCATGAT  1080
ACACAGCCGG  GGCAATCGCT  TGAGTCGACT  GTCCAAACAT  GGTTTAAGCC  GCTTGCTTAC  1140
GCTTTTATTC  TCACAAGGGA  ATCTGGATAC  CCTCAGGTTT  TCTACGGGGA  TATGTACGGG  1200
ACGAAAGGAG  ACTCCCAGCG  CGAAATTCCT  GCCTTGAAAC  ACAAAATTGA  ACCGATCTTA  1260
AAAGCGAGAA  AACAGTATGC  GTACGGAGCA  CAGCATGATT  ATTTCGACCA  CCATGACATT  1320
GTCGGCTGGA  CAAGGGAAGG  CGACAGCTCG  GTTGCAAATT  CAGGTTTGGC  GGCATTAATA  1380
ACAGACGGAC  CCGGTGGGGC  AAAGCGAATG  TATGTCGGCC  GGCAAAACGC  CGGTGAGACA  1440
TGGCATGACA  TTACCGGAAA  CCGTTCGGAG  CCGGTTGTCA  TCAATTCGGA  AGGCTGGGGA  1500
GAGTTTCACG  TAAACGGCGG  GTCGGTTTCA  ATTTATGTTC  AAAGATAGAA  GAGCAGAGAG  1560
GACGGATTTC  CTGAAGGAAA  TCCGTTTTTT  TATTTTGCCC  GTCTTATAAA  TTTCTTTGAT  1620
TACATTTTAT  AATTAATTTT  AACAAAGTGT  CATCAGCCCT  CAGGAAGGAC  TTGCTGACAG  1680
TTTGAATCGC  ATAGGTAAGG  CGGGGATGAA  ATGGCAACGT  TATCTGATGT  AGCAAAGAAA  1740
GCAAATGTGT  CGAAAATGAC  GGTATCGCGG  GTGATCA                             1777
```

PRODUCTION OF ENZYMES IN SEEDS AND THEIR USE

RELATED APPLICATIONS

This application is a Continuation-in-Part U.S. application Ser. No. 07/756,994, filed Sep. 11, 1991, abandoned, which is a Continuation-in Part of U.S. application Ser. No. 07/498,561, filed Mar. 23, 1990, abandoned.

TECHNICAL FIELD

The instant invention pertains to the production of enzymes of interest in the seeds of transgenic plants and the use of the thus-produced seeds in industrial processes, without the need for extraction and/or isolation of the enzyme.

BACKGROUND OF THE INVENTION

A number of industries are using enzymes for their processes. These include detergents, textiles, dairy, food and beverage, feed and other industries.

At the present, enzymes are produced on an industrial scale by fermentation processes or are isolated from plant or animal sources. Microbially produced enzymes include proteases, amylases, cellulases, pectinases, phytases and others. Enzyme production by a fermentation process is highly efficient and production levels of more than 10 grams per liter culture medium can be reached.

The possibility of using transgenic plants as a production system for valuable proteins has been proposed. Examples to date are the production of interferon in tobacco (Goodman et al., 1987), enkephalins in tobacco, *Brassica napus* and *Arabidopsis thaliana* (Vandekerckhove et al., 1989), antibodies in tobacco (Hiatt et al., 1990) and human serum albumin in tobacco and potato (Sijmons et al., 1990).

In practice, the transformation of an increasing number of plant species, especially *dicotyledonous* species (e.g. tobacco, potato, tomato, Petunia, Brassica), has become a routine procedure for workers skilled in the art (Klee et al., 1987; Gasser & Fraley, 1989). Strategies for the expression of foreign genes in plants have become well established (Gasser & Fraley, 1989). Regulatory sequences from plant genes have been identified that are used for the construction of chimeric genes that can be functionally expressed in plants and plant cells.

For the introduction of gene constructions into plants, several technologies are available, such as transformation with *Agrobacterium tumefaciens* or *Agrobacterium rhizogenes*. Using this strategy, a wide variety of plant tissues have been exploited, the choice being largely dependent on the plant species and its amenability in tissue culture. Successful examples are the transformation of protoplasts, microspores or pollen, and explants such as leaves, stems, roots, hypocotyls and cotyls. Furthermore, methods for direct DNA introduction in protoplasts and plant cells or tissues are used such as microinjection, electroporation, particle bombardment and direct DNA uptake (Gasser & Fraley, 1989).

Proteins may be produced in plant seeds using a variety of expression systems. For instance, the use of a constitutive promoter such as the 35S promoter of Cauliflower Mosaic Virus (CaMV) (Guilley et al., 1982) will result in the accumulation of the expressed protein in the seeds, inter alia, of the transgenic plant. Alternatively, use may be made of promoters from genes encoding seed storage proteins. Seed storage proteins are expressed in a highly tissue-specific and stage-specific manner (Higgins, 1984; Shotwell & Larkins, 1989), i.e., the genes are expressed only in seed and only during the stage of seed development.

A seed storage protein (reviewed in Higgins, 1984; Shotwell & Larkins, 1989) is defined as any protein which accumulates in significant quantities (up to 90% of total seed protein) in the developing seed and which on germination is hydrolyzed to provide a nutritional source for the early stages of seedling growth. The proteins are contained in an intracellular compartment called the protein body or storage vacuole. This protein body contains protease inhibitors and creates a protease-free environment. The proteases that degrade the storage proteins become active 3–6 days after germination (Larkins, 1981).

Many seed storage protein genes have been isolated and characterized, as well as their 5' and 3' flanking regions (reviewed by Casey & Domoney, 1987). Examples for the globulins and albumins are the glycinin and conglycinin genes of soybean (Fischer & Goldberg, 1982; Harada et al., 1989), the legumin and vicilin genes from pea (Lycett et al., 1984; Higgins et al., 1988), the 11S field bean gene (Baumlein et al., 1986), the 7S phaseolin gene from Phaseolus (Doyle et al., 1986), the cruciferin and napin genes from Brassica (Ryan et al., 1989; Scofield & Crough, 1987; Radke et al., 1988), the helianthin gene from sunflower (Vonder Haar et al., 1988; Jordano et al., 1989) and the 2S albumin and cruciferin genes from *Arabidopsis thaliana* (Vandekerckhove et al., 1989; Pang et al., 1988). Other examples may be found in the genes encoding the prolamins and glutelins (Casey & Domoney, 1987). Generally, the storage proteins are encoded by multigene families.

Seed storage protein genes have been transferred to tobacco, petunia and rapeseed (Okamura et al., 1986; Beachy et al., 1984; Sengupta-Gopalan et al., 1985; Higgins et al., 1988; Ellis et al., 1988; Barker et al., 1988, Vandekerckhove et al., 1989; Altenbach et al., 1989). The 5' upstream regulatory region of beta-phaseolin from pea was used to direct the expression of beta-glucoronidase (Bustos et al., 1989), phytohemaglutinin (Voelker et al., 1989), luciferase (Riggs et al., 1989) and zein (Hoffman et al., 1987) in tobacco. The promoter of the *Arabidopsis thaliana* 2S albumin gene was used to direct the expression of a modified 2S albumin from the same species in tobacco, *Brassica napus* and *Arabidopsis thaliana* (Vandekerckhove et al., 1989). The genes mentioned above were expressed in a tissue-specific and developmentally regulated manner, i.e., in seed during seed development. The expression levels in all these reports varied, but reached levels as high as 1.7% of the total seed protein (Voelker et al., 1989). It has been found that cDNA can replace genomic DNA containing introns as the basis for obtaining a functional and stable mRNA in the heterologous expression (Chee et al., 1986). These results demonstrate that a person skilled in the art of plant molecular biology can design strategies for seed-specific expression of a given gene in a target plant species that is amenable to transformation technology.

During seed development of dicots, a large part of the total protein synthesis is directed into the vacuole or the protein bodies of storage parenchyma cells. For regulation of this process, the proteins are generally synthesized as precursors. The precursor proteins are equipped with hydrophobic signal peptides, usually at the N-terminus, that are cleaved off at specific stages. A large number of storage protein signal peptides have been described (Doyle et al., 1986; Pang et al., 1988; Vonder Haar et al., 1988; Iturriaga et al., 1989; Dorel et al., 1989; Voelker et al., 1989; Hattori et al., 1985; Lycett et al., 1983; Smith & Raikhel, 1989).

The general applicability of signal peptides in heterologous expressions systems (e.g., Sijmons et al., 1990; Vitale & Bollini, 1986; Slightom et al. 1986; Della-Cioppa et al., 1987) seems to support the idea that a fusion of a signal peptide with a heterologous "passenger protein" may be used for transporting and processing of the passenger protein. The references suggest that a variety of potential "passenger proteins" are candidates for such an expression system.

However, in spite of the attractiveness and viability of the use of plants as bioreactors, the system up until now is not without difficulties. For the examples described above, the plant is used as a bioreactor and the protein of interest is then isolated from the transgenic plant material, i.e., from the tissues containing the highest levels of the protein of interest. The isolation of the protein of interest from the seeds in which it is produced inherently introduces complications as well as added cost (Krebbers & Vandekerckhove, 1990).

A possible solution to this problem may be to avoid the need to extract the expressed protein from the plant material. East German patent DD 275,704 discloses a construct for the expression of a heat stable beta-glucanase in the ungerminated seeds of transformed barley plants and the use of the seeds in brewing processes. However, a persistent problem in the manipulation of small grain cereal crops has been not only the transformation of the protoplasts of cereal plants but the regeneration of the transformed plants as well, which are not enabled in the patent's disclosure. Thus, it would not be possible to obtain enzyme-containing seeds using the process as described in the publication.

SUMMARY OF THE INVENTION

DISCLOSURE OF THE INVENTION

According to the present invention, seeds containing at least one enzyme of interest are provided, which can be used in various industrial processes or in food and feedstuffs as catalysts for digestive reactions, without the need for first extracting and/or isolating said enzymes.

DNA constructs are provided for the transformation of plants which are, in turn, capable of expression of a variety of enzymes of interest in seeds. The constructs employ signal sequences operably linked to a DNA sequence encoding the desired enzyme to be expressed. Such constructs are under the control of regulatory sequences which are capable of directing the expression of the desired enzymes in seeds.

The present invention also provides for the use of the seeds of transgenic plants as a stable and manageable storage form of enzymes. The enzymes are maintained in a dessicated environment which is low in protease activity and thus are protected against degradation.

Moreover, the use of seeds for the storage of enzymes provides a stable vehicle which is easily packaged and transported, and easily handled during actual use.

The present invention further provides a viable solution to the expensive and problematic process of the extraction of enzymes of interest from the seeds in which they are produced. The enzymes remain stable inside the seed and as such may be used as a replacement for the pure enzyme. This benefit, coupled with the low cost of growing seed-producing plants, provides an economical source of such enzymes. Thus, the present invention allows for the reduction of costs associated with the production, storage and use of a variety of enzymes.

DESCRIPTION OF PREFERRED EMBODIMENTS

BRIEF DESCRIPTION OF THE DRAWINGS

FIG. 3 (SEQ ID NO:20) shows the genomic sequence of the seed-storage protein gene cruciferin from *Brassica napus*.

FIG. 4 (SEQ ID NO:21 through SEQ ID NO:32) shows the sequences of synthetic oligonucleotide duplexes used for the various constructions.

FIG. 7 (SEQ ID NO:33) shows the genomic sequence of the α-amylase gene of *Bacillus licheniformis* as present in vector pPROM54.

FIG. 13 is a chromatogram showing a comparison of oligosaccharide patterns obtained from the hydrolysis of corn starch using A) tobacco seeds transformed with the gene encoding *Bacillus licheniformis* α-amylase, B) *Bacillus licheniformis* α-amylase and C) *Bacillus amyloliquefaciens* α-amylase.

DETAILED DESCRIPTION OF THE INVENTION

Figure 1:
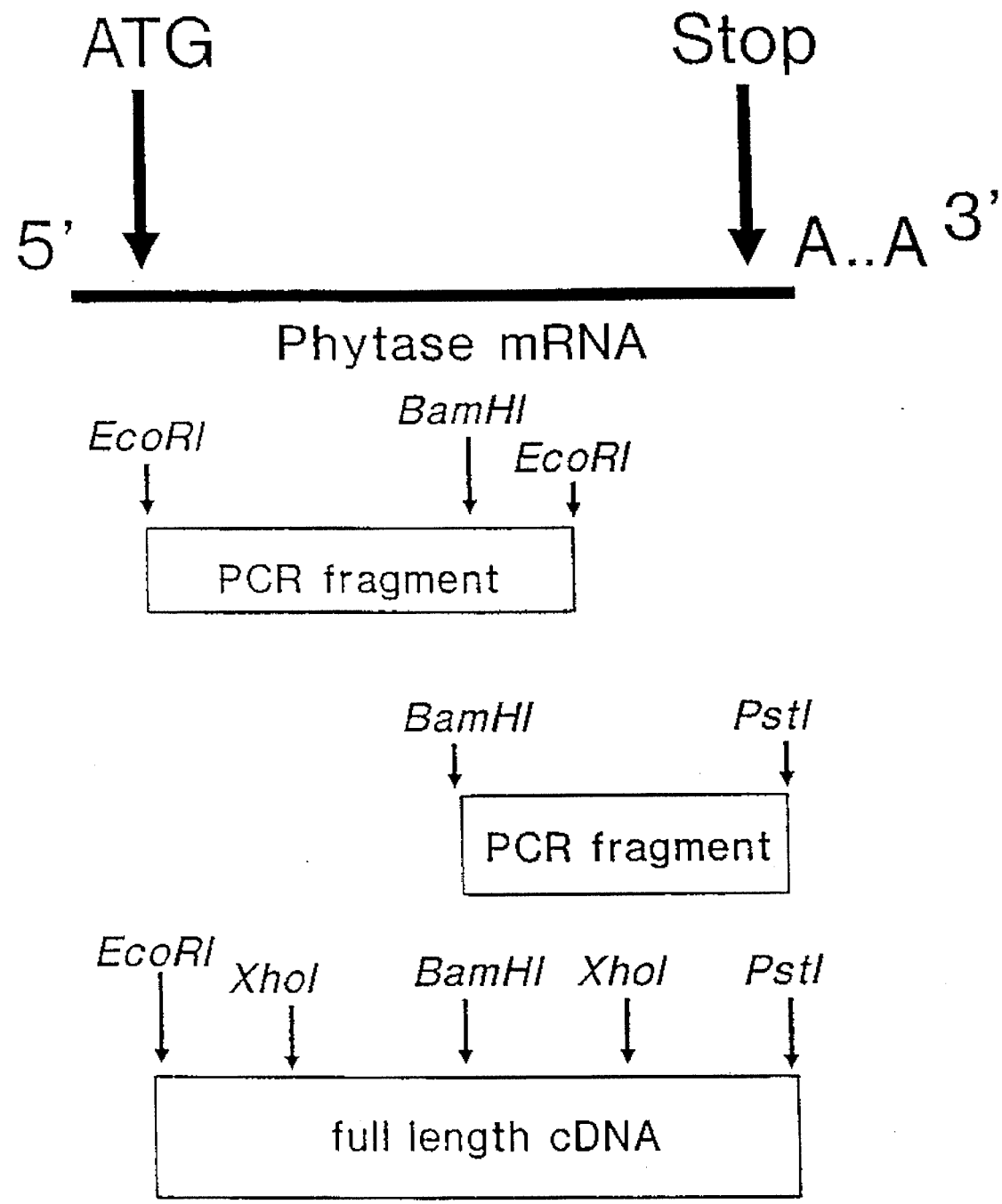
FIG. 1 is a schematic showing the strategy for cloning phytase cDNA.

Enzymes of interest which may be produced by the present invention include any enzymes which are capable of use in an industrial process.

The enzymes of interest include enzymes which are heterologous to the plant (i.e. not native to the plant species) in which they are produced. Also intended are enzymes, homologous to the plants (i.e. native to the plant species) in which they are produced, which are overexpressed via recombinant DNA techniques.

Such enzymes are selected from hydrolases such as proteases, cellulases, hemi-cellulases, phosphatases, lipases, pectinases, amylases, lysozymes, pullulanases and chitinases; lyases such as pectinlyase; and isomerases such as glucose isomerase.

Preferred enzymes are phytase, α-amylase, cellobiohydrolase, endo-glucanase, endo-xylanase, endo-galactanase, α-galactosidase, arabinanase, serine-proteases, chymosin, papain, gastric lipases, pectin lyase and glucose isomerase.

By industrial processes is intended processes in which extracted and/or isolated enzymes are normally included in a reaction mixture, either in vivo or in vitro, containing at least one substrate, wherein the enzymes are capable of catalyzing such reaction of the substrate(s) so as to produce desired effects or products.

Examples of such industrial processes include, but are not limited to, in vitro processes such as the use of phytases in soy processing or in an industrial process such as wet milling or for the production of inositol or inositol-phosphates from phytate. Hemi-cellulases and cellulases may also be used as cell wall degrading enzymes, in general. In a like manner, α-amylases may be used in the baking industry to improve the consistency of baked products; α-amylase, amyloglucosidase, xylanases and/or glucose isomerase may be used in starch liquefaction; ligninases and/or xylanases may be used in the paper industry; glucanases, pectinases and/or cellulases may be used in the food and beverage industry, e.g., in fermentation or brewing processes.

Apart from the above-mentioned action of enzymes in in vitro processes, the enzymes stored in seeds may be used to catalyze digestive reactions in vivo. In this manner, the enzymes facilitate the release of nutrients from foodstuffs which otherwise would not be readily available to the animal which ingests them.

Enzymes to be used in such in vivo processes include, but are not limited to, phytases, cellulases, hemi-cellulases, pectinases and amylases. The enzymes as will lead to improved digestion of the foodstuffs. Enzymes as digestive aids can also be used in humans, for instance in illnesses such as cystic fibrosis or other causes of pancreatic insufficiencies. Lipases, proteases, and cellulases contained in seeds may be used as therapeutic additives to alleviate digestive problems associated with such illnesses.

According to the present invention, the desired enzyme is produced in the seeds of transgenic plants. The thus-produced seeds are in turn used in an industrial process which requires the enzyme contained therein, without the need for first extracting and/or isolating the enzyme.

It will be appreciated by those skilled in the art that seeds containing enzymes for industrial use may be directly used in such processes, or may first be prepared for such use by means of grinding to the desired consistency. In either case, the whole or ground seeds may be fed as such into the desired process without the need for further extraction and/or isolation of the enzyme, and also without loss of activity of the enzyme.

Transgenic plants, as defined in the context of the present invention, include plants and their progeny, which have been genetically modified to cause or enhance production of at least one enzyme of interest in their seeds. The production of the enzymes of interest is thus increased over the level found in the wild-type plant variety.

In the context of the present invention, the phrase "seeds containing an enhanced amount of enzyme" refers specifically to a statistically significant number of seeds which, on average, contain a statistically significant greater amount of an enzyme as compared with the average amount of enzyme in an equal number of non-modified seeds.

Plant genera which are capable of producing the enzyme of interest in their seed by practice of the present invention include, but are not limited to, Nicotiana (e.g., tabacum), Brassica (e.g., napus and oleracea), Arabidopsis, Glycine (e.g., max), Zea (e.g., mays), Amaranthus, Hordeum (e.g., vulgarum), and Pisum (e.g., sativum), Juglans (e.g. regia), Arachis (e.g. hypogeae), Medicago (e.g. sativa), Phaseolus (e.g. vulgaris), Pisum (e.g. sativum), Triticum (e.g. aestivum), Panicum L., Helianthus (e.g. annus), Avena (e.g. sativa) and Oryza (e.g. sativa).

Preferably, the species of choice must have a large production of seed per plant per annum and the chemical and physical properties of the seed should be compatible with the industrial process for which the enzyme is produced. For instance, in some cases when these seeds (after transformation of the parent plant) are to be included in foodstuffs, one may choose a plant species that produces seeds which are low in tannins or other antinutritional factors. In other cases the ability of the transgenic seeds to be ground to the desired consistence may be the criterion of choice when the seeds are used as additives, e.g., in flour. In yet another embodiment, the seeds containing the enzymes of interest may be directly applied to the desired process (e.g. in feedstuffs), per se, optionally preceded by dehusking and/or drying after harvesting.

The choice of the most suitable plant species can be based on reconstitution experiments. The enzyme of interest can be added together with wild-type seeds to the industrial process for which the transgenic seeds will eventually be produced.

The genetic modification of the above-described seed-producing plants intends that an expression construct containing a gene encoding an enzyme of interest is introduced into the target plant. This expression construct may include a gene, heterologous to the plant, which is under the control of promoter and termination regions capable of regulating the expression of the gene encoding the enzyme of interest in the seeds of the plant. Also intended is a gene, homologous to the plant which is under the control of a regulatory region capable of effecting the overproduction of the enzyme of interest. By overproduction is intended production of the enzyme of interest at levels above that which is found in the wild-type plant variety.

Several techniques are available for the introduction of the expression construct containing a DNA sequence encoding an enzyme of interest into the target plants. Such techniques include but are not limited to transformation of protoplasts using the calcium/polyethylene glycol method, electroporation and microinjection or (coated) particle bombardment (Potrykus, 1990).

In addition to these so-called direct DNA transformation methods, transformation systems involving vectors are widely available, such as viral vectors (e.g. from the Cauliflower Mosaic Virus (CaMV)) and bacterial vectors (e.g. from the genus Agrobacterium) (Potrykus, 1990). After selection and/or screening, the protoplasts, cells or plant parts that have been transformed can be regenerated into whole plants, using methods known in the art (Horsch, R. B. et al., 1985). The choice of the transformation and/or regeneration techniques is not critical for this invention.

For dicots, a preferred embodiment of the present invention uses the principle of the binary vector system (Hoekema et al., 1983; Schilperoort et al., 1984) in which Agrobacterium strains are used which contain a vir plasmid with the virulence genes and a compatible plasmid containing the gene construct to be transferred. This vector can replicate in both *E. coli* and in Agrobacterium, and is derived from the binary vector Bin19 (Bevan, 1984) which is altered in details that are not relevant for this invention. The binary vectors as used in this example contain between the left- and right-border sequences of the T-DNA, an identical NPTII-gene coding for kanamycin resistance (Bevan, 1984) and a multiple cloning site to clone in the required gene constructs.

The transformation and regeneration of monocotyledonous crops is not a standard procedure. However, recent scientific progress shows that in principle monocots are amenable to transformation and that fertile transgenic plants can be regenerated from transformed cells. The development of reproducible tissue culture systems for these crops, together with the powerful methods for introduction of genetic material into plant cells has facilitated transformation. Presently the methods of choice for transformation of monocots are microprojectile bombardment of explants or suspension cells, and direct DNA uptake or electroporation of protoplasts. For example, transgenic rice plants have been successfully obtained using the bacterial hph gene, encoding hygromycin resistance, as a selection marker. The gene was introduced by electroporation (Shimamoto et al., 1989). Transgenic maize plants have been obtained by introducing the *Streptomyces hygroscopicus bar* gene, which encodes phosphinothricin acetyltransferase (an enzyme which inactivates the herbicide phosphinothricin), into embryogenic cells of a maize suspension culture by microparticle bombardment (Gordon-Kamm et al., 1990). The introduction of genetic material into aleurone protoplasts of other monocot crops such as wheat and barley has been reported (Lee et al., 1989). Wheat plants have been regenerated from embryogenic suspension culture by selecting only the aged compact and nodular embryogenic callus tissues for the establishment of the embryogenic suspension cultures (Vasil et al., 1990). The combination with transformation systems for these crops enables the application of the present invention to monocots. These methods may also be applied for the transformation and regeneration of dicots.

The expression of recombinant genes in plants involves such details as transcription of the gene by plant polymerases, translation of mRNA, etc., which are known to persons skilled in the art of recombinant DNA techniques. Only details relevant for the proper understanding of this invention are discussed below.

Regulatory sequences which are known or are found to cause sufficiently high expression (for the purpose of the specific application, as discussed below) of the recombinant DNA in seeds, can be used in the present invention. Such regulatory sequences may be obtained from plants or plant viruses, or chemically synthesized. Such regulatory sequences are promoters active in directing transcription in seeds. These include, but are not limited to, promoters from seed-specific genes, especially those of storage protein genes, such as the cruA promoter of *Brassica napus* (Ryan et al., 1989) or promoters of constitutively expressed genes, such as the 35S promoter of CaMV (Cauliflower Mosaic Virus) (Guilley et al., 1982). Other regulatory sequences are terminator sequences and polyadenylation signals, including every sequence functioning as such in plants; examples are the 3' flanking region of the nopaline synthase gene of *Agrobacterium tumefaciens* or the 3' flanking region of the cruA gene of *Brassica napus*. The regulatory sequences may also include enhancer sequences, such as found in the 35S promoter of CaMV, and mRNA stabilizing sequences such as the leader sequence of Alfalfa Mosaic Virus (AlMV) RNA4 (Brederode et al., 1980) or any other sequences functioning as such.

The protein of interest should be in an environment that allows optimal stability of the protein during seed maturation. The choice of cellular compartments, such as cytosol, endoplasmic reticulum, vacuole, protein body or periplasmic space can be used in the present invention to create such a stable environment, depending on the biophysical parameters of the protein of interest. Such parameters include, but are not limited to, pH-optimum, sensitivity to proteases or sensitivity to the molarity of the preferred compartment. Although homologous signal sequences are preferred, heterologous signal sequences may be used as well. Especially preferred are signal sequences obtained from seed storage proteins.

The seed storage proteins can be divided into four major classes based on solubility characteristics:

1. Albumins—soluble in water and subdivided in two main classes (12S and 2S). The 12S class includes lectins isolated from pea and various beans, e.g., 2S albumins from *Brassica napus, Arabidopsis thaliana, Ricinus communis* (castor bean), *Bertholletia excelsa* (Brazil nut), pea, radish and sunflower.

2. Globulins-soluble in salt solutions and may be either of the 7–8S class like the phaseolins from Phaseolus, the vicilins from pea, the conglycinins from soybean, the oat-vicilins from oat and 7S globulins from other species, or of the 11–14S class such as the legumins from pea, the glycinins from soybean, the helianthins from sunflower, the cruciferins from rape or 11–14S proteins from other species such as Arabidopsis and bean.

3. Prolamins—soluble in aqueous alcohol, e.g., zeins from corn, the hordeins from barley, the gliadins isolated from wheat and the kafirins from sorghum.

4. Glutelins—soluble in acidic or alkaline solutions and may be isolated from wheat.

Although there are exceptions, the major storage proteins in seed of dicotyledonous plants are globulins, and those of monocotyledonous plants are prolamins and glutelins.

All parts of the relevant DNA constructs (promoters; regulatory, stabilizing, signal or termination sequences) of the present invention may be modified, if desired, to affect their control characteristics using methods known to those skilled in the art. The amount of recombinant protein (the "expression level") needed in the seed should be sufficiently high to use the transgenic seed as a minor additive (on a volume, weight or cost base) in all preferred embodiments of the present invention.

A number of methods may be used to obtain transgenic plants of which the seeds contain more than one enzyme of interest. These include, but are not limited to:

a. Cross-fertilization of transgenic plants expressing one or more enzymes of interest.

b. Plant transformation with a DNA fragment or plasmid that contains multiple genes encoding enzymes of interest, using the necessary regulatory sequences.

c. Plant transformation with different DNA fragments or plasmids simultaneously, each containing a gene for an enzyme of interest, using the necessary regulatory sequences.

d. Successive transformation of plants, each time using a DNA fragment or plasmid encoding a different enzyme of interest under the control of the necessary regulatory sequences.

c. A combination of the methods mentioned above.

The actual method used to obtain seeds which contain more than one enzyme of interest is not critical with respect to the objective of this invention.

It is pointed out that seeds containing enhanced amounts of enzymes could be obtained by processes, known to those skilled in the art, other than those recombinant processes mentioned above provided those processes result in obtaining seeds with enhanced amounts of enzymes as compared with the wild-type seeds. For example, it might be possible to obtain such seeds by the use of somaclonal variation techniques. Further, such techniques could be used by themselves or in combination with breeding techniques which employ the concept of cytoplasmic male sterility (Cms) or nuclear male sterility (Nms) (Mariani et al., 1990). Techniques such as somaclonal variation and cross-breeding involving the use of Cms or Nms could be used in combination with the recombinant technologies mentioned above in order to further increase the relative amounts of enzymes present within the seeds. With respect to non recombinant techniques which might be utilized to enhance the amount of enzymes within seeds reference is made to U.S. Pat. No. 4,378,655 issued 7 Apr. 1983 which patent is incorporated herein by reference to disclose such techniques. It is pointed out that there are numerous publications describing breeding techniques involving cytoplasmic male sterility which was discovered by P. LeClercq in 1968 and the corresponding dominant fertility restoring genes (Rf) which were discovered by M. L. Kinmar et al. in 1970. Recently, the use of nuclear male sterility has been described by Mariani et al. in 1990. More generalized disclosures relating to plant breeding are discussed within James R. Welsh "Fundamentals of Plant Genetics and Breeding", 1981 as well as within J. M. Poehlman, "Breeding Field Crops", 1959.

In one embodiment of the present invention, a double-stranded cDNA encoding phytase is prepared from mRNA isolated from *Aspergillus ficuum* (van Gorcom et al., 1991). The DNA construct is placed under the control of regulatory sequences from the 12S storage protein cruciferin from *Brassica napus*. The construct is thereafter subcloned into a binary vector such as pMOG23 (in *E. coli* K-12 strain DH5α, deposited at the Centraal Bureau voor Schimmelcultures, Baarn, the Netherlands on Jan. 29, 1990, under accession number CBS 102.90). This vector is introduced into *Agrobacterium tumefaciens* which contains a disarmed Ti plasmid. Bacterial cells containing this construct are cocultivated with tissues from tobacco or Brassica plants, and transformed plant cells are selected by nutrient media containing antibiotics and induced to regenerate into differentiated plants on such media. The resulting plants produce seeds that contain and express the DNA construct.

In another embodiment of the present invention, the phytase-encoding DNA construct is placed under the control of regulatory sequences from the 35S promoter of Cauliflower Mosaic Virus (CaMV). The construct is thereafter subcloned into a binary vector. This vector is then introduced into *Agrobacterium tumefaciens* which contains a disarmed Ti plasmid. Bacterial cells containing this construct are co-cultivated with tissues from tobacco or Brassica plants, and transformed plant cells are selected by nutrient media containing antibiotics and induced to regenerate into differentiated plants on such media. The resulting plants contain and express the DNA construct constitutively.

The phytase enzyme activity of the transgenic seeds may be determined by a variety of methods, not critical to the present invention, such as an ELISA assay, Western blotting or direct enzyme assays using colorimetric techniques or native gel assays.

The seeds containing the thus-produced phytase can be used in industrial processes such as in feed additives for nonruminants, in soy processing, or in the production of inositol or inositol phosphates from phytate. If necessary or desired, the seeds may first be ground to the desired consistency before use, depending on the nature of the industrial process, without the need for further extraction and/or isolation of the phytase. One of ordinary skill in the art may determine whether such preparatory steps are necessary.

Phytase produced in seed can also be used in a process for steeping corn or sorghum kernels. Seeds may be ground before adding to steeping corn. Phytase liberated from the seeds can act on phytin, which is present in many corn preparations. Degradation of phytin in steeping corn is beneficial for the added commercial value of corn steep liquor, which is used as animal feed or as a nutrient in microbial fermentations. Furthermore, the degradation of phytin can prevent problems relating to the accumulation of deposits in filters, pipes, reactor vessels, etc., during concentration, transport and storage of corn steep liquor (Vaara et al., 1989). The action of phytase can also accelerate the steeping process and the separation processes involved in corn wet milling.

In yet another embodiment of the present invention, a genomic DNA fragment encoding α-amylase from *Bacillus licheniformis* is placed under the control of the CaMV 35S promoter and enhancer sequences. The mRNA stabilizing leader sequence of RNA4 from AlMV is included, as well as the terminator and polyadenylation signal sequences of the nopaline synthase gene of *Agrobacterium tumefaciens*. The entire construct is thereafter subcloned into a binary vector. This vector is introduced into *Agrobacterium tumefaciens* which contains a disarmed Ti plasmid. Bacterial cells containing this construct are cocultivated with tissues from tobacco plants, and transformed plant cells are selected by nutrient media containing antibiotics and induced to regenerate into differentiated plants on such media. The resulting plants produce seeds that contain and express the DNA construct.

The α-amylase enzyme activity of the transgenic seeds may be determined via methods, not critical to the present invention, such as direct enzyme assays using colorimetric techniques or native gel assays.

The seeds can be used as a source of α-amylase, which can be directly used in industrial processes, such as the preparation of starch syrups. Preferably, the seeds are first ground and the entire (ground) mixture may be used in the process, as may be determined by one of ordinary skill in the art.

The following examples are provided so as a to give those of ordinary skill in the art a complete disclosure and description of how to make and use the invention and are not intended to limit the scope of what the inventors regard as their invention. Efforts have been made to ensure accuracy with respect to numbers used (e.g., amounts, temperature, pH, etc.) but some experimental errors and deviation should be accounted for. Unless indicated otherwise, temperature is in degrees Centigrade and pressure is at or near atmospheric.

EXAMPLE 1

Isolation of poly A$^+$ RNA From *Aspergillus ficuum*

*A. ficuum* strain NRRL 3135 is grown in a medium containing 22.72 g/l maize flour (amylase treated at pH 7 at 85° C. during 15 minutes), 9.36 g/l glucose, 2.9 g/l KNO$_3$, 0.142 g/l KCl, 0.142 g/l MgSO$_4$.7H$_2$O and 56.8 mg/l FeSO$_4$.7H$_2$O. After 6 days the mycelium is harvested.

Dry mycelium (0.5 g) is frozen with liquid nitrogen and ground. Subsequently, the material is homogenized with an Ultra turrax (full speed, 1 minute) at 0° C. in 3M LiCl, 6M urea and maintained overnight at 4° C. as described by Auffray & Rougeon (1980). Total cellular RNA is obtained after centrifugation at 16,000×g followed by two successive extractions with phenol:chloroform:isoamyl alcohol (50:48:2). The RNA is precipitated with ethanol and redissolved in 1 ml 10 mM Tris-HCl (pH 7.4), 0.5% SDS. For poly A$^+$ selection, the total RNA sample is heated for 5 minutes at 65° C., adjusted to 0.5M NaCl and subsequently applied to an oligo(dT)-cellulose column. After several washes with a solution containing 10 mM Tris pH 7.0, 1 mM EDTA and 0.1 mM NaCl, the poly A$^+$ RNA is collected by elution with 10 mM Tris pH 7.0 and 1 mM EDTA.

EXAMPLE 2

Preparation and Cloning of a cDNA Encoding Phytase

For the synthesis of the first strand of the cDNA 5 μg of poly A$^+$ RNA, isolated according to Example 1, is dissolved in 16.5 μl H$_2$O and the following components are added: 2.5 μl RNasin (30 U/μl), 10 μl of a buffer containing 50 mM Tris-HCl pH 7.6, 6 mM MgCl$_2$ and 40 mM KCl, 2 μl 1M KCl, 5 μl 0.1M DTT, 0.5 μl oligo(dT)$_{12-18}$ (2.5 mg/ml), 5 μl 8 mM dNTP-mix, 5 μl BSA (1 mg/ml) and 2.5 μl Moloney MLV reverse transcriptase (200 U/μl). The mixture is incubated for 30 minutes at 37° C. and the reaction is stopped by addition of 10 μl 0.2M EDTA and 50 μl H$_2$O. An extraction is performed using 110 μl chloroform and after centrifugation for 5 minutes 5M NH$_4$Ac and 440 μl absolute ethanol (−20° C.) are added to the aqueous layer. Precipitation is done in a dry ice/ethanol solution for 30 minutes. After centrifugation (10 minutes at 0° C.), the cDNA/mRNA pellet is washed with 70% ice-cold ethanol. The pellet is dried and dissolved in 20 μl of H$_2$O.

Isolation of the cDNA encoding phytase is performed with the polymerase chain reaction (PCR) in two fragments. The two fragments are combined, using the BamHI site within the gene to create a full-length cDNA. The strategy for the cloning of the phytase cDNA is shown in FIG. 1.

Sequencing of the phytase gene (van Gorcom et al., 1991) reveals the presence of a BamHI site at approximately 800 basepairs from the initiation codon. The nucleotide sequence around this BamHI site, as well as the nucleotide sequence preceding the start codon and the nucleotide sequence after the stop codon of the phytase gene are used to design oligonucleotides for the PCR.

The polymerase chain reaction is performed according to the supplier of Taq-polymerase (cetus) using 1.5 μl of the solution containing the reaction product of the first strand synthesis and 0.5 μg of each of the oligonucleotides. Amplification is performed in a DNA amplifier of Perkin Elmer/Cetus. After 25 cycles of 2 minutes at 94° C., 2 minutes at 55° C., and 3 minutes at 72° C., the reaction mixture is deproteinized by subsequent phenol and chloroform extractions. The DNA is precipitated, redissolved in a buffer containing 10 mM Tris, pH 7 and 0.1 mM EDTA and subsequently digested with suitable restriction enzymes.

For the amplification of the fragment encoding the N-terminal part of the protein, the two following oligonucleotides are used:

Oligo 1: 5' GGGTAGAATTCAAAAATGGGCGTCTCT-GCTGTTCTA 3' (SEQ ID NO:1)

Oligo 2: 5' AGTGACGAATTCGTGCTGGTGGAGATG-GTGTCG 3' (SEQ ID NO:2)

The amplified fragment is digested with EcoRI and cloned into the EcoRI site of pTZ18R (purchased from Pharmacia). Restriction site mapping and nucleotide sequencing demonstrate the authenticity of the fragment. The resulting plasmid is named pGB925.

For the amplification of the second fragment, the following two oligonucleotides are used:

Oligo 3: 5' GAGCACCAAGCTGAAGGATCC 3' (SEQ ID NO:3)

Oligo 4: 5' AAACTGCAGGCGTTGAGTGTGATTGTT-TAAAGGG 3' (SEQ ID NO:4)

The amplified fragment is digested with BamHI and PstI and subsequently cloned into pTZ18R, which has been digested with BamHI and PstI. Restriction site mapping and nucleotide sequencing show that the correct fragment is isolated. The resulting plasmid is named pGB926.

In order to isolate a full-length cDNA, pGB925 is digested with EcoRI and BamHI and the fragment containing the phytase-encoding DNA is isolated. This fragment is cloned into plasmid pGB926 which has been digested with EcoRI and BamHI, resulting in plasmid pGB927. Plasmid pGB927 contains a full-length cDNA encoding phytase, with an approximate size of 1.8 kbp.

EXAMPLE 3

Construction of the Binary Vector pMOG23

In this example, the construction of the binary vector pMOG23 (in *E. coli* K12 DH5α, deposited at the Centraal Bureau voor Schimmel-cultures on Jan. 29, 1990 under accession number CBS 102.90) is described.

Figure 2:
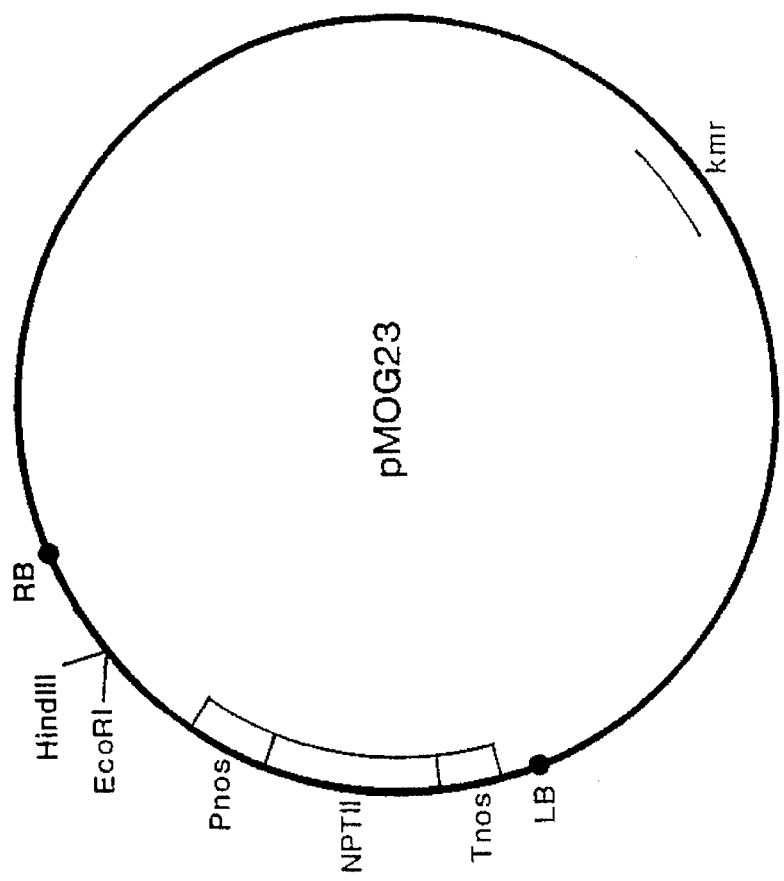
FIG. 2 (SEQ ID NO:19) is a diagram of binary vector pMOG23.

The binary vector pMOG23 (FIG. 2) is a derivative of vector Bin19 (Bevan, M., 1984). To obtain pMOG23, the vector Bin19 is changed in a way not essential for the present invention, using techniques familiar to those skilled in the art of molecular biology.

First, the positions of the left border (LB) and the right border (RB) are switched with reference to the neomycine phosphotransferase gene II (NPTII gene). Secondly, the orientation of the NPTII gene is reversed giving transcription in the direction of LB. Finally, the polylinker of Bin19 is replaced by a polylinker with the following restriction enzyme recognition sites: EcoRI, KpnI, SmaI, BamHI, XbaI, SacI, XhOI, and HindIII.

EXAMPLE 4

Cloning of the Phytase cDNA of *Aspergillus ficuum* in an Expression Construct for Constitutive Expression in Plants The phytase gene from *Aspergillus ficuum* is tailored and cloned in an expression construct for constitutive expression downstream of the Cauliflower Mosaic Virus 35S promoter. The expression construct also contains the coding information for a signal peptide sequence of plant origin.

The phytase cDNA is cloned into the expression construct as present on plasmid pMOG29 (described under a)). Subsequently the entire construct is introduced into the binary vector pMOG23 and transferred to *Agrobacterium tumefaciens* strain LBA4404.

a) Construction of expression vector pMOG29

Figure 8:
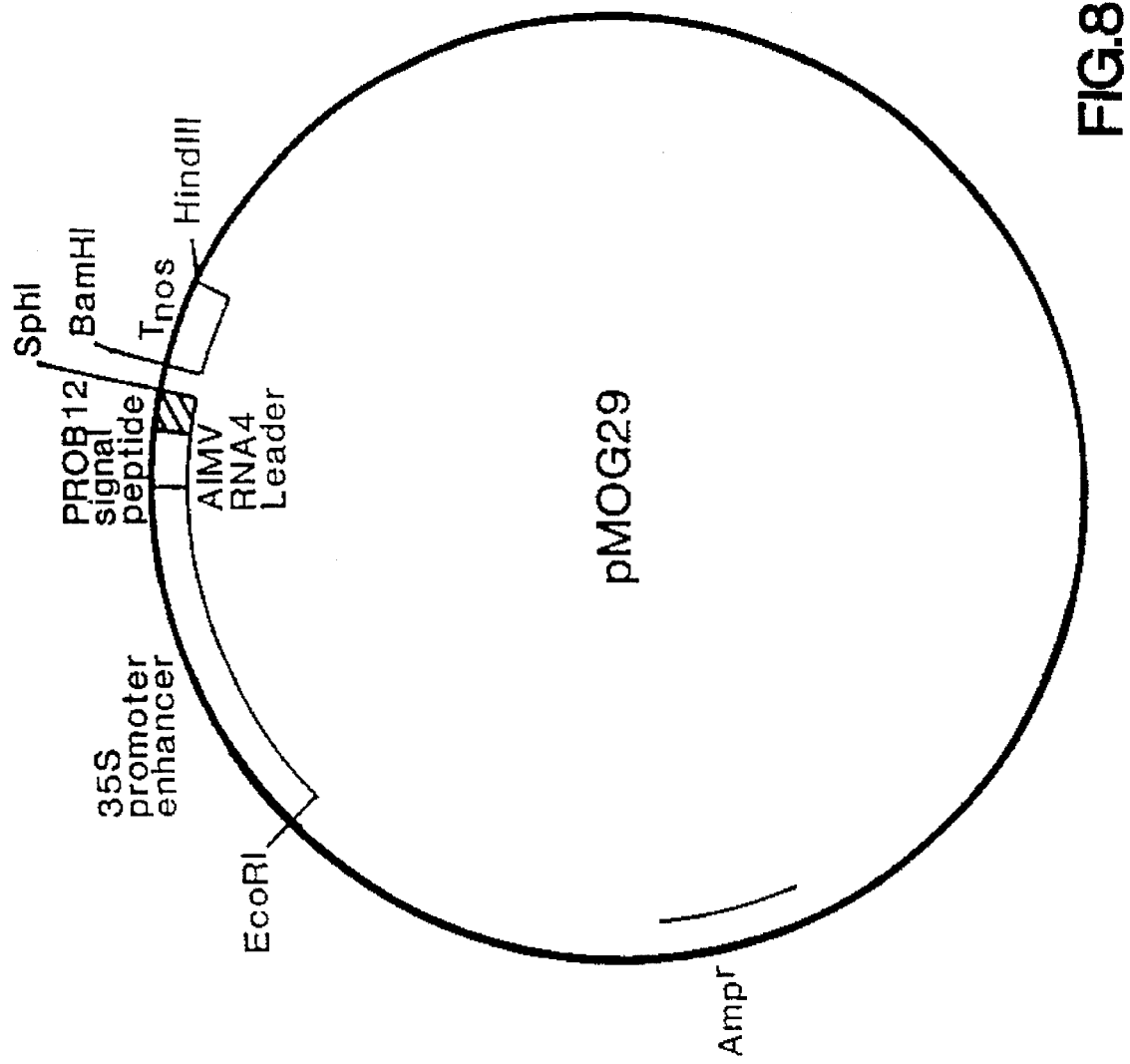
FIG. 8 is a diagram of plasmid pMOG29. Plasmid pUC18 containing an expression cassette for constitutive expression in plants and a sequence encoding a tobacco signal peptide.

The expression construct of ROK1 (Baulcombe et al., 1986) is cloned as an EcoRI/HindIII fragment into pUC18. This construct contains the Cauliflower Mosaic Virus (CaMV) 35S promoter on an EcoRI/BamHI fragment and the nopaline synthase (nos) transcription terminator on a BamHI/HindIII fragment. The promoter fragment consists of the sequence from −800 to +1 of the CaMV 35S promoter. Position +1, which is included, is the transcription initiation site (Guilley et al., 1982). The sequence upstream of the NcoI site at position −512 is deleted and this site is changed into an EcoRI site. This is done by cutting the expression construct present in pUC18 with NcoI, filling in the single-stranded ends with Klenow polymerase and ligation of an EcoRI linker. The resulting plasmid is cut with EcoRI, resulting in the deletion of the EcoRI fragment carrying the sequences of the 35S promoter upstream of the original NcoI site. The BamHI/HindIII fragment, containing the nos terminator is replaced by a synthetic DNA fragment (oligonucleotide duplex A, FIG. 4) containing the leader sequence of RNA4 of Alfalfa Mosaic Virus (AlMV) (Brederode et al., 1980). This is done by cleavage with BamHI, followed by cleavage with HindIII and ligation of the synthetic DNA fragment. The BamHI site and three upstream nucleotides are deleted by site-directed mutagenesis. In the resulting plasmid, the BamHI/HindIII fragment containing the nos terminator sequence is reintroduced. The gene encoding β-glucuronidase (originating from plasmid pRAJ 275; Jefferson, 1987) was ligated in as an NcoI/BamHI fragment, resulting in plasmid pMOG14. From the literature it is known that duplication of the sequence between −343 and −90 increases the activity of the 35S promoter (Kay et al., 1987). To obtain a promoter fragment with a double, so-called enhancer sequence, the following steps, known to those skilled in the art, are carried out. From plasmid pMOG14, the enhancer fragment is isolated on an AccI/EcoRI fragment and subsequently blunt-ended with Klenow polymerase. The obtained fragment is introduced in pMOG14 cut with EcoRI and blunt-ended, in such a way that the border between the blunt-ended EcoRI and AccI sites generate a new EcoRI site. The resulting plasmid (pMOG18) contains the 35S promoter with a double enhancer sequence, the leader sequence of RNA4 from AlMV and the nos terminator in an expression construct still present on an EcoRI/HindIII fragment. Finally, the NcoI/BamHI fragment encoding β-glucuronidase is replaced with the synthetic DNA fragment B (FIG. 4), derived from the PROB12 cDNA (Cornelissen et al., 1986). This fragment B encodes the PR-protein PR-S signal peptide sequence from tobacco Samsun NN. An SphI site is created in the signal peptide encoding DNA sequence by changing one nucleotide. This change does not alter the amino acid sequence of the encoded PR-S signal peptide. The resulting plasmid is called pMOG29 (FIG. 8).

b) Cloning of the phytase gene from *Aspergillus ficuum* in the binary vector

Oligonucleotide duplex C (FIG. 4) is cloned into plasmid pMOG29, digested with SphI and BamHI, resulting in plasmid pMOG407. The oligonucleotide duplex contains the coding information for the final 2 amino acids of the signal peptide of PR-S, followed by the first 6 amino acids of mature phytase.

The plasmid pGB927, which contains the full length phytase cDNA, is digested with XhoI (partially) and PstI. The XhoI/PstI fragment comprising the DNA sequences encoding mature phytase from amino acid 6 onward is cloned into plasmid pMOG407 linearized with XhoI and PstI, resulting in plasmid pMOG417. The entire construct, containing the chimaeric phytase gene, is inserted as an EcoRI/HindIII fragment into the binary vector pMOG23 linearized with EcoRI and HindIII. The resulting binary plasmid pMOG413 is mobilized, in a triparental mating with the *E. coli* K-12 strain RK2013 (containing plasmid pRK2013) (Ditta et al., 1980), into *Agrobacterium tumefaciens* strain LBA4404 that contains a plasmid with the virulence genes necessary for T-DNA transfer to the plant.

EXAMPLE 5

Transient Expression of a Chimaeric Phytase Gene in Tobacco Protoplasts

Protoplasts of tobacco are transformed with plasmid DNA carrying the chimaeric phytase gene under regulation of the constitutive CaMV 35S promoter. After 72 hours treated protoplasts are assayed for transient expression of the introduced phytase gene using the phytase activity assay.

Protoplasts are prepared from axenically grown 1–2 months old tobacco plants (*Nicotiana tabacum* SR1). The entire procedure is described by Rodenburg et al. (1989). For transformation a number of $5 \cdot 10^5$ protoplasts is electroporated with 40 μg DNA of plasmid pMOG417). After electroporation protoplasts are resuspended in 3 ml of K3G medium. For the phytase activity assay protoplasts are pelleted and the 3 ml of supernatant is dialyzed overnight against an excess of water. The dialysate is freeze-dried and resuspended in 300 μl 25 mM sodium-acetate pH 5.5. The assay is then carried out as described in detail in Example 10, with the only exception that instead of the 250 mM Glycine HCl buffer pH 2.5, a 25 mM sodium acetate buffer pH 5.5. is used.

In these experiments, one phytase unit is defined as 1 μM phosphate released from 1.5 mM sodium phytate solution per minute at 37° C. at pH 5.5.

In untreated protoplasts no detectable activity is found. Protoplasts electroporated with plasmid pMOG417 show an activity of 0.26 PTU (Phytase units, see Example 10) per mg protein in the supernatant.

EXAMPLE 6

Stable Expression of a Chimaeric Phytase Gene in Tobacco Plants Under the Control of the CaMV 35S Promoter Tobacco is transformed by cocultivation of plant tissue with *Agrobacterium tumefaciens* strain LBA4404 containing the binary vector pMOG413 with the chimaeric phytase gene under regulation of the CaMV 35S promoter. Transformation is carried out using cocultivation of tobacco (*Nicotiana tabacum* SR1) leaf discs according to Horsch et al. (1985). Transgenic plants are regenerated from shoots that grow on selection medium (100 mg/l) kanamycin), rooted and transferred to soil. Young plants are assayed for NPTII-activity (kanamycin resistance), grown to maturity and allowed to self-pollenate and set seed.

To determine the phytase activity found in the transgenic seeds, about 50 mg is taken and homogenized with a pestle in an ice-cold mortar in 1 ml 25 mM sodium-acetate buffer pH 5.5. After centrifugation, the supernatant is assayed as described for the transient assays. In 32 independently transformed tobacco plants, a maximum phytase expression level of 0.4% of the total soluble seed protein was observed. No phytase activity could be detected in untransformed plants.

Two transgenic plant lines, 413.25 and 413.32, were selected on the basis of their high expression levels of phytase (approximately 0.4%) in seeds.

EXAMPLE 7

Cloning of the Phytase cDNA of *Aspergillus ficuum* in a Seed-specific Expression Construct An expression construct is constructed in such a way that seed-specific expression is obtained, using sequences of the *Brassica napus* 12S storage protein gene cruciferin (cruA; Ryan et al., 1989). These sequences may be replaced by those from similar seed-specific genes to achieve the same goal as is the objective of this invention.

The phytase cDNA is cloned into the expression construct. Finally, the entire construct is introduced into *Agrobacterium tumefaciens*, which is used for transformation. In case of any other protein of interest cloning of the gene or cDNA is done in essentially the same way as described here for the phytase cDNA.

For all *E. coli* transformations in this example, *E. coli* K-12 strain $DH_5\alpha$ is used.

a) Construction of the expression construct

For the construction of the expression construct for seed-specific expression, the promoter and terminator sequences from the cruciferin A (cruA) gene of *Brassica napus* cv. Jet Neuf are synthesized using PCR technology with isolated genomic DNA (Mettler, I. J., 1987) as a template. This gene shows seed-specific expression and its coding and flanking sequences have been determined (Ryan et al., 1989).

Two sets of oligonucleotides are synthesized. One to allow amplification of the cruA 5' flanking region and part of the signal peptide encoding sequence as an EcoRI/NcoI fragment:

5' GTTCGGAATTCGGGTTCCGG 3' (SEQ ID NO:5) and
5' AACTGTTGAGCTGTAGAGCC 3' (SEQ ID NO:6).

The other for amplification of the 3' flanking sequence as a BglII/HindIII fragment:

5' CTTAAGATCTTACCCAGTGA 3' (SEQ ID NO:7) and 5' CGGAGAAGCTTGCATCTCGT 3' (SEQ ID NO:8).

The oligo's are designed to contain suitable restriction sites at their termini to allow direct assembly of the expression construct after digestion of the fragments with the restriction enzymes.

The 5' fragment of the cruA gene, that includes 54 nucleotides of the sequence encoding the signal peptide is cloned into vector pMOG445 (Oligonucleotide duplex E (FIG. 4) cloned into vector pUC18, linearized with SstI and EcoRI), cut with EcoRI and NcoI, resulting in vector pMOG424. The synthetic oligonucleotide duplex D (FIG. 4), comprising the final 5 coding triplets for the signal sequence of *Brassica napus* cruciferin, the sequence encoding amino acids 1–6 of mature phytase and a multiple cloning site, is cloned in vector pMOG424 cut with NcoI and HindIII. The resulting vector is called pMOG425. The 3' cruA PCR fragment is cloned as a BglII/HindIII fragment into pMOG425 digested with BglII and HindIII, resulting in pMOG426.

b) Cloning of the phytase gene from *Aspergillus ficuum* in the binary vector

Figure 5:
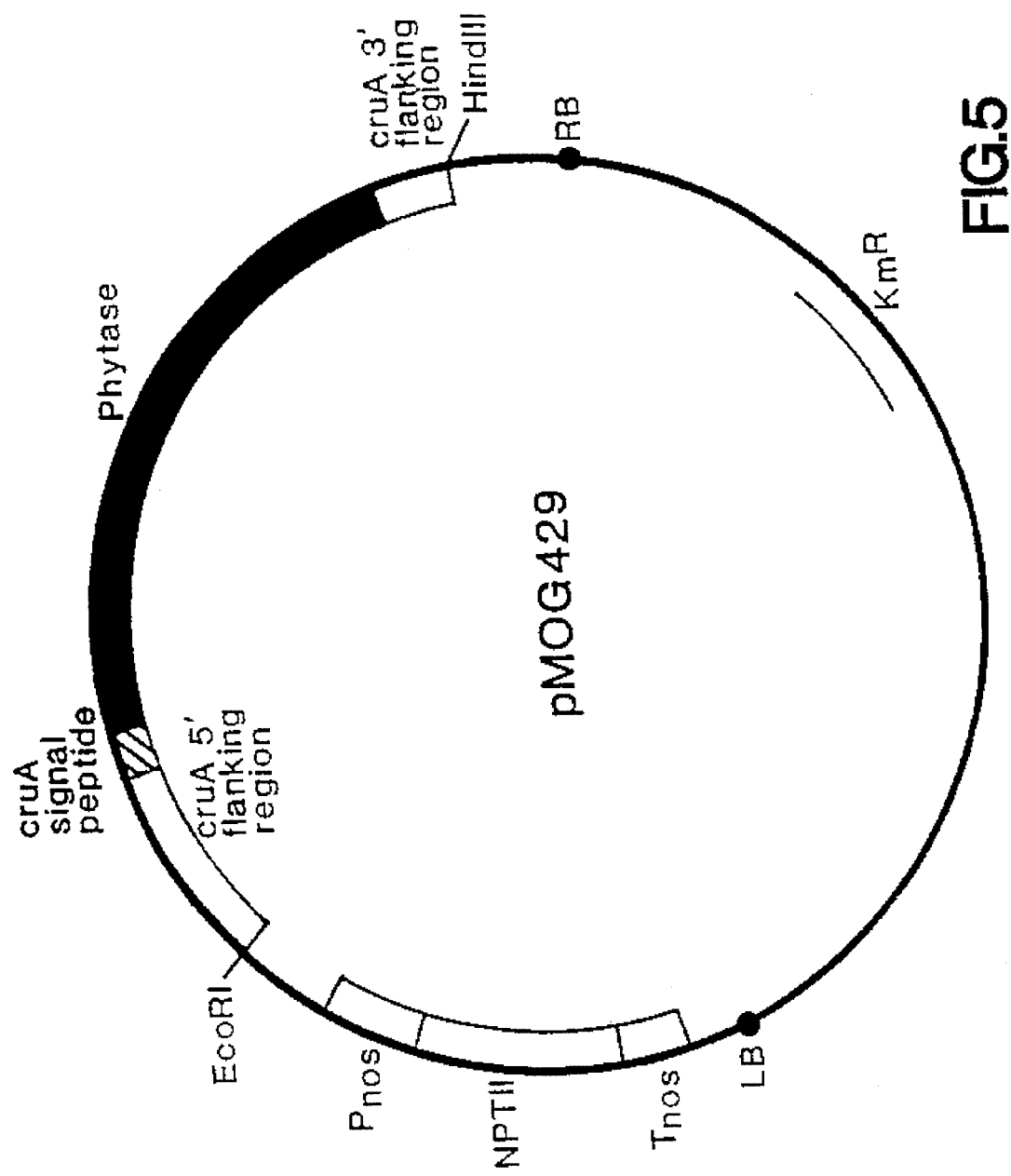
FIG. 5 is a diagram of plasmid pMOG429. Binary vector pMOG23 containing the cDNA part of phytase encoding the mature enzyme downstream of a DNA sequence encoding the cruciferin signal peptide.

Plasmid pGB927, which contains the full-length coding sequence for *Aspergillus ficuum* phytase, is digested with XhoI (partially) and with PstI. The XhoI/PstI fragment comprising the DNA sequences encoding mature phytase from amino acid 6 onward is cloned in vector pMOG426, cut with XhoI and PstI. From the resulting vector pMOG428, the entire construct, containing the chimeric phytase gene, is inserted as an EcoRI/HindIII fragment in the binary vector pMOG23 linearized with EcoRI and HindIII. The resulting binary vector pMOG429 (FIG. 5) is mobilized, in a triparental mating with the *E. coli* K-12 strain RK2013 (containing plasmid pRK2013) (Ditta et al., supra), into Agrobacterium strain LBA4404 (Hoekema et al., 1983, supra) which contains a plasmid with the virulence genes necessary for T-DNA tranfer to the plant.

EXAMPLE 8

Stable Seed-specific Expression of Phytase in Tobacco Seeds Under the Control of a Cruciferin Promoter Agrobacterium strain LBA4404, containing the binary vector pMOG429 with the phytase cDNA under the control of the cruciferin promoter, is used for transformation experiments. Transformation of tobacco (*Nicotiana tabacum* SR1) is carried out using co-cultivation of leaf discs according to the procedure of Horsch et al. (1985). Transgenic plants are regenerated from shoots that grow on selection medium (100 mg/l kanamycin). Young plants are assayed for NPTII-activity (kanamycin resistance), grown to maturity and allowed to self-pollenate and set seed. Seeds from individual transformants are pooled and part of the seed sample is assayed for the presence of phytase. From clones with the highest expression levels, compared to untransformed control seeds, the remaining seeds are germinated on kanamycin (200 mg/L) (hence also transgenic for phytase) and selected and used for mass propagation of plants capable of producing the highest amounts of phytase in their seeds. These can then be used, e.g. for digestion experiments.

To determine the phytase activity found in the transgenic seeds, about 50 mg seed is taken and homogenized with a pestle in an ice-cold mortar in 1 ml 25 mM sodium-acetate buffer pH 5.5. After centrifugation, the supernatant is assayed as described for the transient assays. In 55 independently transformed tobacco plants, a maximum phytase expression level of 0.15% of the total soluble seed protein was observed. Phytase activity was not detected in stems, roots and leaves of the transgenic plants. No phytase activity could be detected in untransformed plants.

EXAMPLE 9

Transformation of Rapeseed

In this example, the transformation of rapeseed by co-cultivation of plant tissue with *Agrobacterium tumefaciens*, containing a binary vector with the chimeric phytase gene is described. Transgenic plants may be selected on antibiotic resistance. The transgenic plants may be assayed for phytase activity. High expressors may be analyzed more thoroughly and used in further experiments.

The same chimeric phytase construct in a binary vector (pMOG429) is mobilized into *Agrobacterium tumefaciens* strain LBA4404, in a like manner as described in Example 7. This strain may be used to transform rapeseed (*Brassica napus* cv. Westar). To this aim, surface-sterilized stem segments taken from 5 to 6 week-old plants, just before flowering, are preconditioned for 24 h on MS medium (Fry et al., 1987) with 1 mg/l BAP and then co-cultivated for 48 h with Agrobacterium on fresh plates with the same medium. Transgenic plantlets may be regenerated from shoots that grow on selection medium (500 mg/l carbenicilline, 40 mg/l paromomycin) and further analyzed as described in example 8 for tobacco.

EXAMPLE 10

Phytase Activity Assay

A total of 25 mg of seeds from *Nicotiana tabacum* plant line 413.25 which in total contain approximately 0.25 PTU were ground. (PTU=Phytase units. One unit of phytase activity is defined as that amount of enzyme which liberates inorganic phosphorus from 1.5 mM sodium phytate at the rate of 1 μmol/min at 37° C. and at pH 2.5).

The ground seed is incubated in a total volume of 50 ml of a 250 mM glycine/HCl buffer pH 2.5 containing 0.86 g sodium phytate.11 $H_2O$. Although Aspergillus phytase expresses a pH optimum at 2.5 as well as at 5.5, the lower pH is chosen to exclude plant phytase activity.

The resulting mixture is incubated for 15 and 60 minutes at 37° C. The reaction is stopped by the addition of 5 ml from the incubate into 5 ml of 10% TCA (trichloroacetic acid). Thereafter, 10 ml of indicator reagent (3.66 g $FeSO_2.7H_2O$ in 50 ml of ammonium molybdate solution (2.5 g $(NH_4)6Mo_7O_{24}.4H_2O$ and 8 ml conc. $H_2SO_4$, diluted up to 250 ml with demi water)) is added to the stopped enzyme solution. The intensity of the blue color is measured spectrophotometrically at 700 nm.

The inorganic phosphate content present at T=0 serves as a blank.

The measurements are indicative of the quantity of phosphate released in relation to a calibration curve of phosphate in the range of 0–1 mM.

EXAMPLE 11

Incubation of Ground *Nicotiana tabacum* Seeds with Feedstuffs

In a typical experiment, 0.25 g of solvent extracted soybean meal is incubated with 25 mg of ground *Nicotiana tabacum* seeds (plant line 413.25) containing approximately 0.25 PTU as described above, except for the addition of sodium phytate. In this case, the added incubation agent consists of a mixture of 410 ml buffer and 90 ml of demi water.

Figure 6:
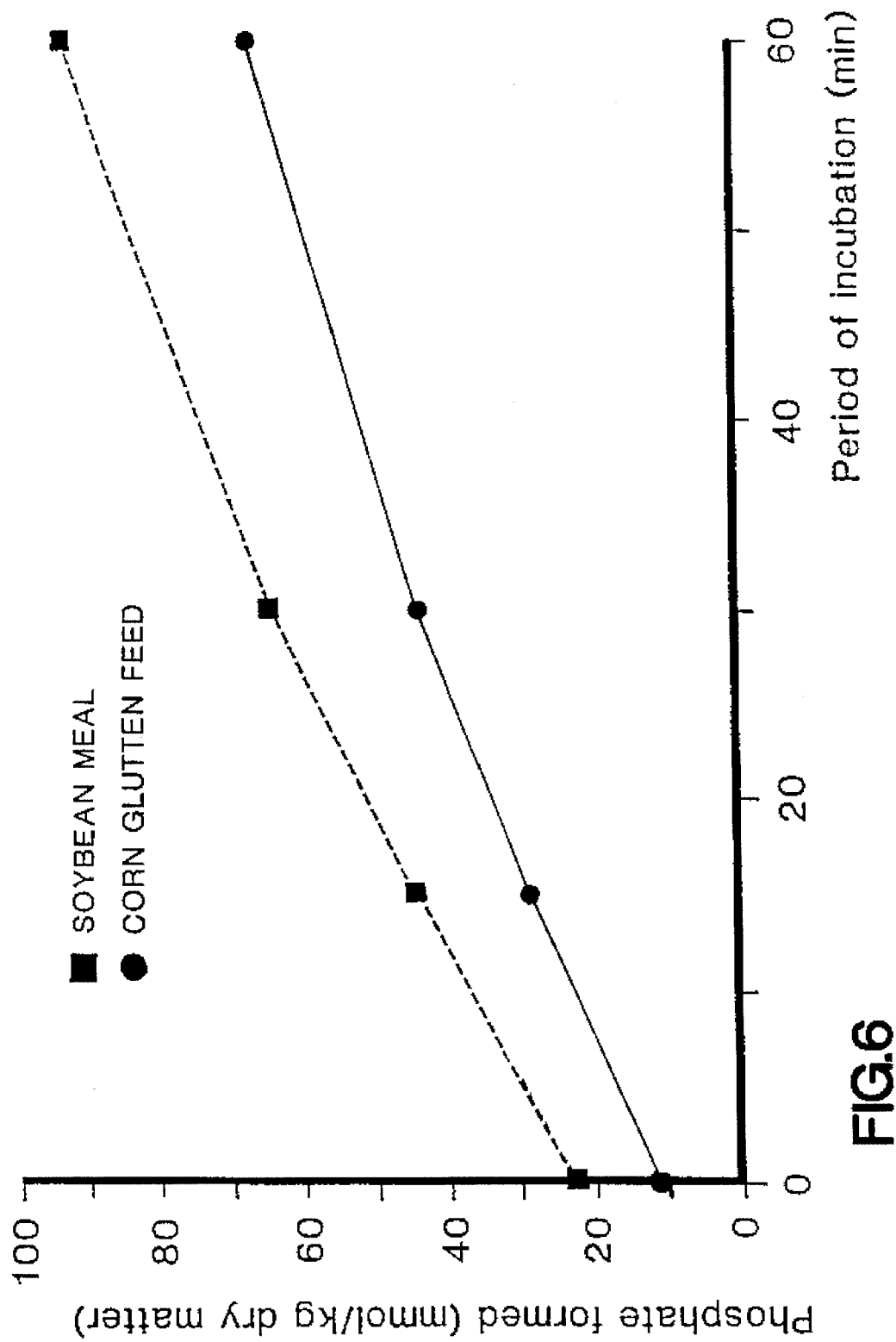
FIG. 6 is a graph showing the effects of the addition of ground seeds containing phytase on the liberation of inorganic phosphorous from phytate.

The liberation of phosphate from phytate in solvent extracted soybean meal is depicted in FIG. 6. Without added ground seeds, no activity is observed.

In a virtually identical experiment, similar results are obtained using maize gluten feed as a substrate. Results are shown in FIG. 6.

No activity is observed in the absence of ground seeds or when ground seeds are added which do not contain phytase activity.

EXAMPLE 12

In Vitro Testing of Transgenic Seeds Containing Phytase Under Conditions Simulating the Digestive Tract of Poultry To assess the effectivity of phytase produced in transgenic tobacco seeds, the activity of phytase from Aspergillus is determined in a model simulating the conditions found in the digestive tract in poultry.

A standard poultry feed sample is first incubated at 1 g/15 ml demi water for 60 minutes at 39° C. to simulate the conditions in the crop of the animals. Subsequently, 5 ml of a pepsin solution (Merck: 5.28 g/l, pH 3.0—adjusted with HCl) is added, the pH adjusted with HCl to pH 3.0, and the incubation is continued for a further 90 minutes at the same temperature to simulate the conditions in the stomach.

During the incubation period, samples were taken in order to determine the amount of phosphate released from the phytate present in the feed.

Figure 10:
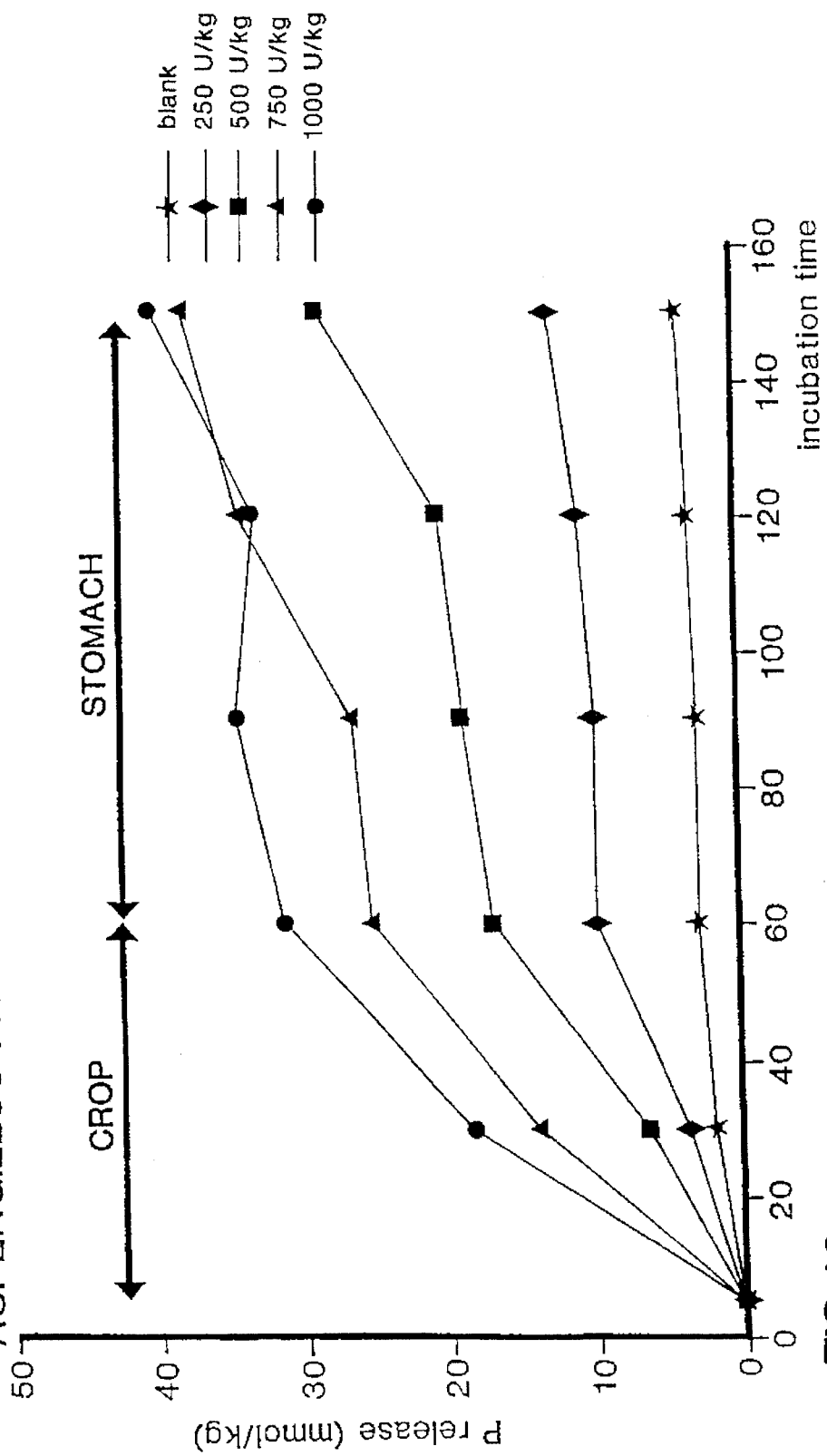
FIG. 10 is a graph showing the dose-response relationship of Aspergillus phytase in an in vitro digestion model.

The action of fungal phytase is apparent from FIG. 10. Increasing the phytase dosage from 250 to 1000 PTU/kg feed results in an increased release of phosphate from the feed sample.

Figure 11:
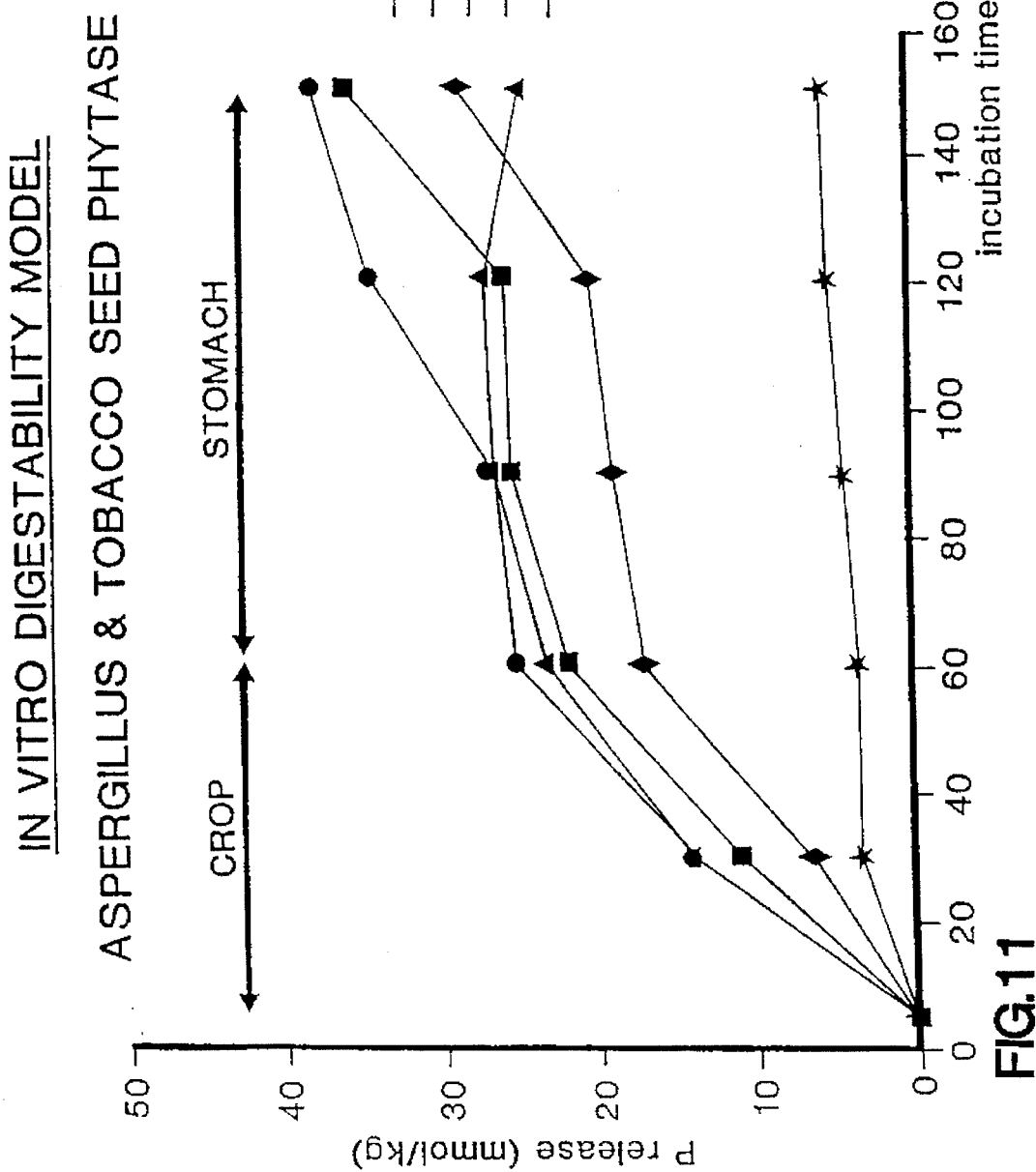
FIG. 11 is a graph showing the dose-response relationship of Aspergillus phytase and phytase contained in tobacco seed in an in vitro digestion model.

When a sample of transgenic tobacco seed (lines 413.25 or 413.32; after grinding in a mortar) is added in place of the fungal phytase, a similar increased phosphate release is observed (FIG. 11). Control tobacco seed, which did not contain phytase, was also tested. No phosphate release was observed as compared to the blank control.

Comparison of the results with 50 g transgenic tobacco seed/kg feed with those obtained with 500 and 750 PTU/kg feed indicates that 1 g tobacco seed equals approximately 12 PTU in this in vitro poultry digestion model.

EXAMPLE 13

Animal Testing

Trials are carried out with broilers to show the efficacy of phytase expressed in plant seeds, as well as the absence of any negative effect of seeds from tobacco on zootechnical results.

Phytase-expressing tobacco seeds and control seed are harvested. Seeds were ground in 100 gram portions with a sieve (Retch-mill ZM1) having pores of 500 μm, taking care to keep the seeds cooled.

One day old male broiler chicks (Hybro) are housed in two tier battery cages (0.45 $m^2$). The ambient temperature is 32° C. during the first two days and is decreased by 4° C. in the first week. Every following week, the temperature is decreased by 2° C. Broilers are reared in a one hour light and three hours dark regime.

The birds are vaccinated against New Castle Disease at one day of age using Clone 30 vaccine. During the experiments, the broilers are fed the experimental diets all mash and ad libitum. Growth and feed/gain ratios are measured during the experimental periods. Apparent availability of total phosphorus is measured in a three day period, during which feed consumption is measured as dry matter intake and excreta are collected quantitatively.

Apparent availability of phosphorus is defined as the difference between intake of phosphorus and excretion of phosphorus with the excreta.

The following control diets without addition of phytase are used:

| Diets | Ca (%) | total P (%) | phytate P (%) |
|---|---|---|---|
| 1 | 0.60 | 0.45 | 0.30 |
| 2 | 0.75 | 0.60 | 0.30 |
| 3 | 0.90 | 0.75 | 0.30 |

No graded feed phosphate is added to diet 1 (basal diet). Calcium and phosphorus from a mixture of anhydrous dicalcium phosphate and monoammonium phosphate (ratio 5:1) are supplemented to diets 2 and 3. All experimental diets are obtained by additions to the basal diet (see Table 1).

Experimental diet 4 contains microbial phytase at a concentration of 400 PTU/kg feed, prepared as described by Van Gorcom et al. (1991).

Experimental diet 5 is like diet 4 but ground seeds of non-transgenic tobacco are added to the feed mixture to achieve a final ratio of 3 kg/90 kg feed.

Experimental diet 6 is also like diet 4 but 3 kg ground seeds of transgenic tobacco (line 413.25) are added to a mixture of 90 kg feed to obtain a final concentration of 400 PTU/kg feed.

The experiment is carried out with 176 broilers in 16 battery cages (11 per battery cage) until the age of 24 days. The treatments (diets) are repeated twice and are assigned randomly to the cages within each tier.

The availability of phosphorus is measured from 21–24 days of age.

The results with regard to phosphorous availability and growth of the animals supplied with diets 4, 5 and 6 each show the positive effect of the addition of phytase (Table 2). A comparison of diets 4, 5 and 6 also demonstrates that the inclusion of tobacco seeds in feed is compatible with the action of microbial phytase in the gastro-intestinal tract of farm animals such as broilers and shows no negative effect on the zootechnical results.

TABLE 1

Composition of Basal Diet in Experiments With Broilers

| Ingredients | Contents (g/kg) |
|---|---|
| Yellow maize | 280.0 |
| Sorghum (low tannin) | 200.0 |
| Sunflower seed meal (solv. extr.) | 80.0 |
| Soya bean meal (solvent extr., 48.8% protein) | 350.0 |
| Soya bean oil | 58.5 |
| Vitamins* | 5.0 |
| Minerals* | 15.0 |
| Limestone | 1.0 |
| Synth. methionine | 1.0 |
| $Cr_2O_3$ | 0.5 |
| | 1001.0 |
| ME (MJ/kg) | 13.1 |
| Lysine | 12.9 |
| Methionine + cystine | 9.1 |
| Calcium | 6.0 (6.0–6.6)** |
| Total phosphorus | 4.5 (4.7–4.7)** |
| Organic phytic phosporus | 3.0 (3.1–3.1)** |

*Amount supplied per kg diet: 12000 IU vitamin A; 2000 IU vitamin $D_3$; 5 IU vitamin E; 1.5 mg vitamin $K_3$; 1 mg thiamine; 5 mg riboflavin; 1 mg pyridoxine; 30 mg nicotinic acid, 7.5 mg D-pantothenic acid; 0.015 mg vitamin $B_{12}$; 0.5 mg folic acid; 350 mg choline chloride; 75 mg ethoxyquin; 9.5 g $CaCO_3$; 2.5 g NaCl; 0.25 g $FeSO_4$; 0.24 g $MnSO_4$; 45 mg $CuSO_4$; 60 mg $ZnSO_4$; 105 mg KI mixture.
**( ) Analyzed for experiments 1 and 2 respectively.

EXAMPLE 14

Cloning of the α-amylase Gene of *Bacillus licheniformis* in an Expression Cassette for Constitutive Expression In this example, the α-amylase gene from *Bacillus licheniformis* is tailored and cloned in an expression cassette for constitutive expression which also contains the coding information for a signal peptide sequence of plant origin. As a final step, the entire construct is cloned in a binary vector, transferred to *Agrobacterium tumefaciens* strain LBA4404, which is used to transform the plant of interest. Any other gene or cDNA may be cloned in a similar way as is described here for the α-amylase gene.

All transformations in this example are done in *E. coli* K-12 strain DH5-α.

a) Tailoring of the α-amylase Gene of *Bacillus licheniformis*

The α-amylase gene from *Bacillus licheniformis* (FIG. 7), present in the Bacillus vector pPROM54 (deposited at the Centraal Bureau voor Schimmelcultures on Nov. 5, 1985, under accession number CBS 696.85), is digested with XbaI and BclI. The XbaI/BclI fragment is cloned in plasmid pUC18 linearized with XbaI and BamHI, resulting in plasmid pMOG318. A SalI/BamHI fragment is synthesized using PCR technology with pMOG318 as a template creating the BamHI site by use of a mismatch primer (indicated in FIG. 7). The SalI/BamHI PCR fragment is cloned in plasmid pIC-19R (Marsh et al., 1984) digested with SalI and BamHI, resulting in plasmid pMOG319. The SalI fragment, which contains the 5' end of the α-amylase gene, from pMOG318 (using the SalI site present in pUC18) is cloned in pMOG319 linearized with SalI. This results in plasmid pMOG320 that contains the entire α-amylase gene.

b) Construction of vector pMOG29

Vector pMOG29 was constructed as described in Example 4(a).

c) Cloning of the α-amylase gene from *Bacillus licheniformis* in the binary vector Plasmid pMOG320 is digested with HgaI and BamHI. The HgaI/BamHI fragment, which encodes mature α-amylase from amino acid 9 onward, is cloned in a three-way ligation with the synthetic oligonucleotide duplex F (FIG. 4) into pMOG29 linearized with SphI and BamHI, resulting in plasmid pMOG321. The oligonucleotide duplex has the coding information for the final 2 amino acids of the signal peptide of PR-S and for the first 9 amino acids of mature α-amylase. The entire construct, containing the chimeric α-amylase gene, is inserted as an EcoRI/HindIII into the

TABLE 2

Effect of Phytase on the Apparent Availability of Total P and Ca, the P Content in Manure and the Performance of Broilers

| | | | Availability (%) 21–24 d | | | Growth 0–24 d |
|---|---|---|---|---|---|---|
| Diets | Ca/P (g/kg) | Added phytase (units/kg) | P | Ca | Amount of P in manure (g) per kg dm feed intake | (g) |
| 1 | 6/4.5 | 0 | 49.8 | 47.2 | 2.7 | 338 |
| 2 | 7.5/6 | 0 | 45.6 | 48.9 | 3.8 | 592 |
| 3 | 9/7.5 | 0 | 44.6 | 46.9 | 4.9 | 683 |
| 4 | as 1 | 400 | 60.5 | 58.6 | 2.1 | 620 |
| 5 | as 1 | 0 | 48.5 | 48.0 | 2.7 | 340 |
| 6 | as 1 | 400 | 60.2 | 59.3 | 2.1 | 615 | binary vector pMOG23 linearized with EcORI and HindIII.

Figure 9:
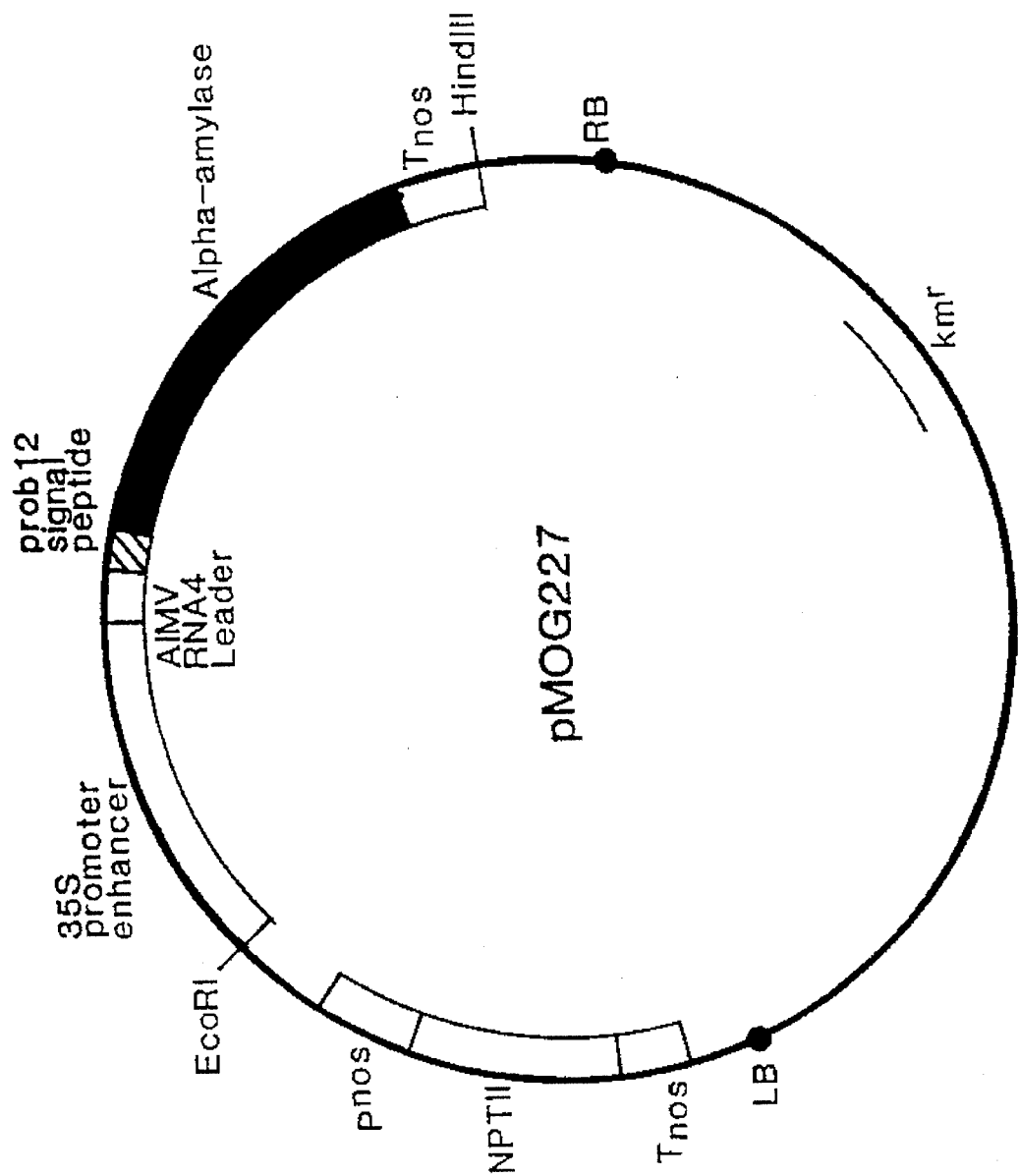
FIG. 9 is a diagram of plasmid pMOG227. Binary vector containing the part of the α-amylase gene encoding the mature enzyme downstream of a tobacco sequence encoding a signal peptide in an expression cassette for constitutive expression.

The resulting binary plasmid pMOG227 (FIG. 9) is mobilized, in a triparental mating with the *E. coli* K-12 strain RK2013 (containing plasmid pRK2013) (Ditta et al., 1980), into Agrobacterium strain LBA4404 that contains a plasmid with the virulence genes necessary for T-DNA tranfer to the plant.

EXAMPLE 15

Stable Expression of *Bacillus licheniformis* α-amylase in Tobacco

In this example tobacco is transformed by cocultivation of plant tissue with *Agrobacterium tumefaciens*, containing a binary vector with the chimeric α-amylase gene. Transgenic plants are selected on antibiotic resistance. The seeds of the transgenic plants are assayed for α-amylase activity. High expressors are analyzed more thoroughly and used in further experiments.

Agrobacterium strain LBA4404 (pMOG227) is used for transformation experiments. Transformation of tobacco (*Nicotiana tabacum* SR1) is carried out using cocultivation of leaf discs according to the procedure of Horsch et al., (1985). Transgenic plants are regenerated from shoots that grow on selection medium (100 mg/l kanamycin). Young plants are assayed for NPTII-activity, grown to maturity and allowed to self-pollenate and set seed. Seeds from individual transformants are pooled and part of the seed sample is assayed for the presence of α-amylase. From clones with the highest expression levels, compared to untransformed control seeds, the remaining seeds are germinated on kanamycin (200 mg/L) (hence also transgenic for α-amylase) and selected and used for mass propagation of plants capable of producing seeds containing the highest amounts of α-amylase. A maximun α-amylase expression level of 0.4% of the total soluble seed protein was observed. These seeds can then be used, e.g. for digestion experiments.

EXAMPLE 16

Application of α-amylase Formulated in Seeds for the Liquefaction of Starch

*Bacillus licheniformis* α-amylase, expressed in tobacco seed, was applied in the liquefaction of starch as follows: 100 grams of both α-amylase-expressing and control tobacco seeds were harvested. Seeds were ground with a sieve (Retch-mill ZM1) having pores of 250 μm, taking care to keep the seeds cooled. To determine their α-amylase content, the milled seeds were extracted with 10 volumes of 0.5M glycine buffer pH 9.0 with 10 mM $CaCl_2$ during 30 min at 0° C. The supernatant was used for α-amylase determination by the Phadebas method (Pharmacia Diagnostics). The units are referred to as TAU (thermostable α-amylase units).

Liquefaction tests were carried out as follows: starch slurry (composition: 3.3 kg corn or potato starch, D.S. (Dry Substance) 88% (2.904 kg starch); 5.45 l $H_2O$; D.S. of slurry becomes 33%; the pH was corrected to 6.5 with 1N sulfuronic acid or 1N NaOH. Either milled seeds or microbial α-amylase were added to an amount equivalent to 4.4 T.A.U./g D.S.) is heated to 100° C. as rapidly as possible and this temperature is maintained for 10 minutes. The slurry is then brought to 95° C. and maintained at that temperature for 2 hours. Afterwards, the samples were acidified with $H_2SO_4$ to obtain pH 3.5 and placed in a boiling water bath for 10 minutes in order to stop enzymatic activity before the DE (dextrose equivalents) and hydrolysis pattern were determined by HPLC. A column of BIORAD HPX-42A was used for HPLC analysis with demineralized water as eluent.

Figure 12C:
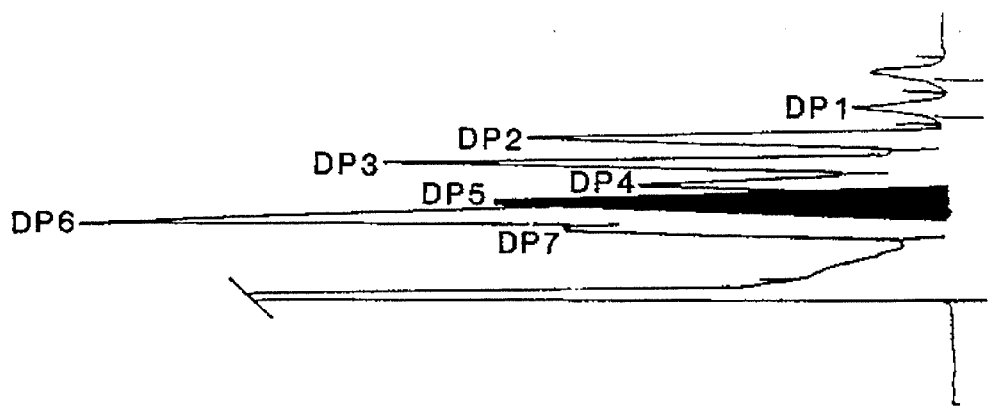
FIG. 12 is a chromatogram showing a comparison of oligosaccharide patterns obtained from the hydrolysis of potato starch using A) tobacco seeds transformed with the gene encoding *Bacillus licheniformis* α-amylase, B) *Bacillus licheniformis* α-amylase and C) *Bacillus amyloliquefaciens* α-amylase.
Figure 12B:
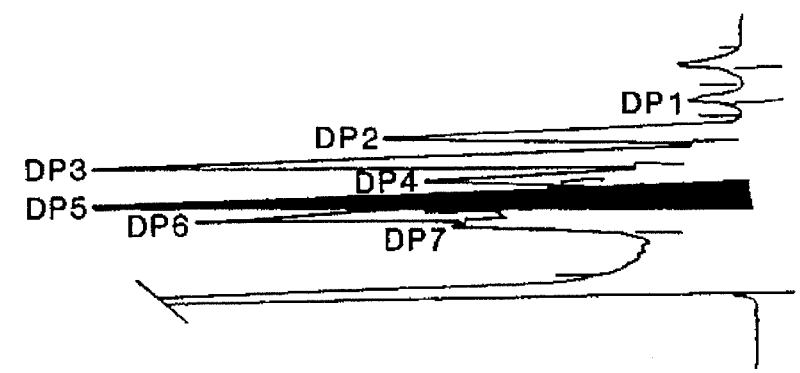
Figure 12A:
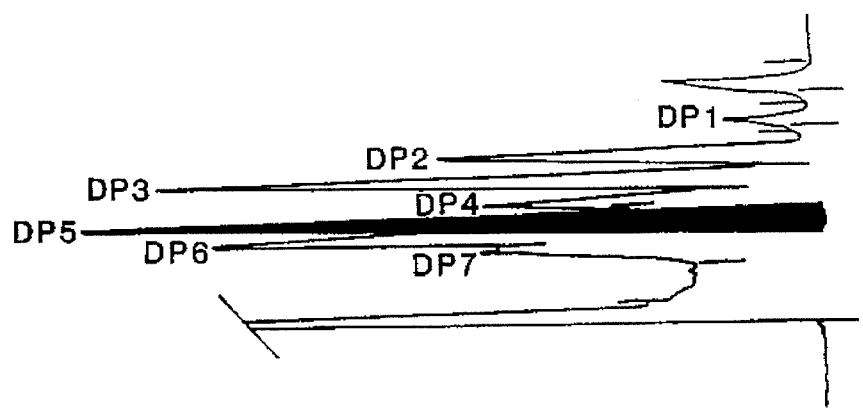

The oligosaccharide pattern obtained from the hydrolysis of potato and corn starch using A) transformed plant seeds; B) Maxamyl$^R$ (*Bacillus licheniformis* α-amylase obtained from Gist-brocades N.V., Delft, The Netherlands); and C) Dexlo$^R$CL (*Bacillus amyloliquefaciens* α-amylase from Gist-brocades) were compared (FIGS. 12 and 13). The oligosaccharide pattern obtained from transformed plant seeds and Maxamyl$^R$ are identical, yet both differ from that obtained from Dexlo$^R$, confirming that *Bacillus licheniformis* α-amylase is produced in plant seeds. The DE values obtained with the plant seeds (Table 3) are in the commercially acceptable range (DE≧12, preferably DE≧16) (Reilly, 1985).

TABLE 3

Dextrose equivalent (DE) values obtained from hydrolysis of corn and potato starch

| | Potato Starch DE | Corn Starch DE |
|---|---|---|
| Maxamyl ® WL7000 | 18 | 16 |
| Transformed tobacco seeds | 16 | 13 |
| Non-transformed tobacco seeds | 0 | 0 |
| Dexlo ® CL | 15 | 18 |

EXAMPLE 17

Stability of Enzymes Produced in Seeds

The storage stability of phytase and α-amylase produced in tobacco seeds were determined at various time intervals and at different storage temperatures.

a) Storage stability of α-amylase produced in tobacco seeds

S2 tobacco seeds of *Nicotiana tabacum* SR1 which has been transformed with the plasmid pMOG227 (see Example 15), in which α-amylase from *Bacillus licheniformis* was expressed extracellularly, were stored at 10° C. α-Amylase activity was determined at two time points with an interval of 18 months. The activity in seeds was 1.3 U/μg soluble protein at both time points, which shows the stability of the enzyme in seed.

b) Storage stability of phytase produced in tobacco seeds

Figure 14:
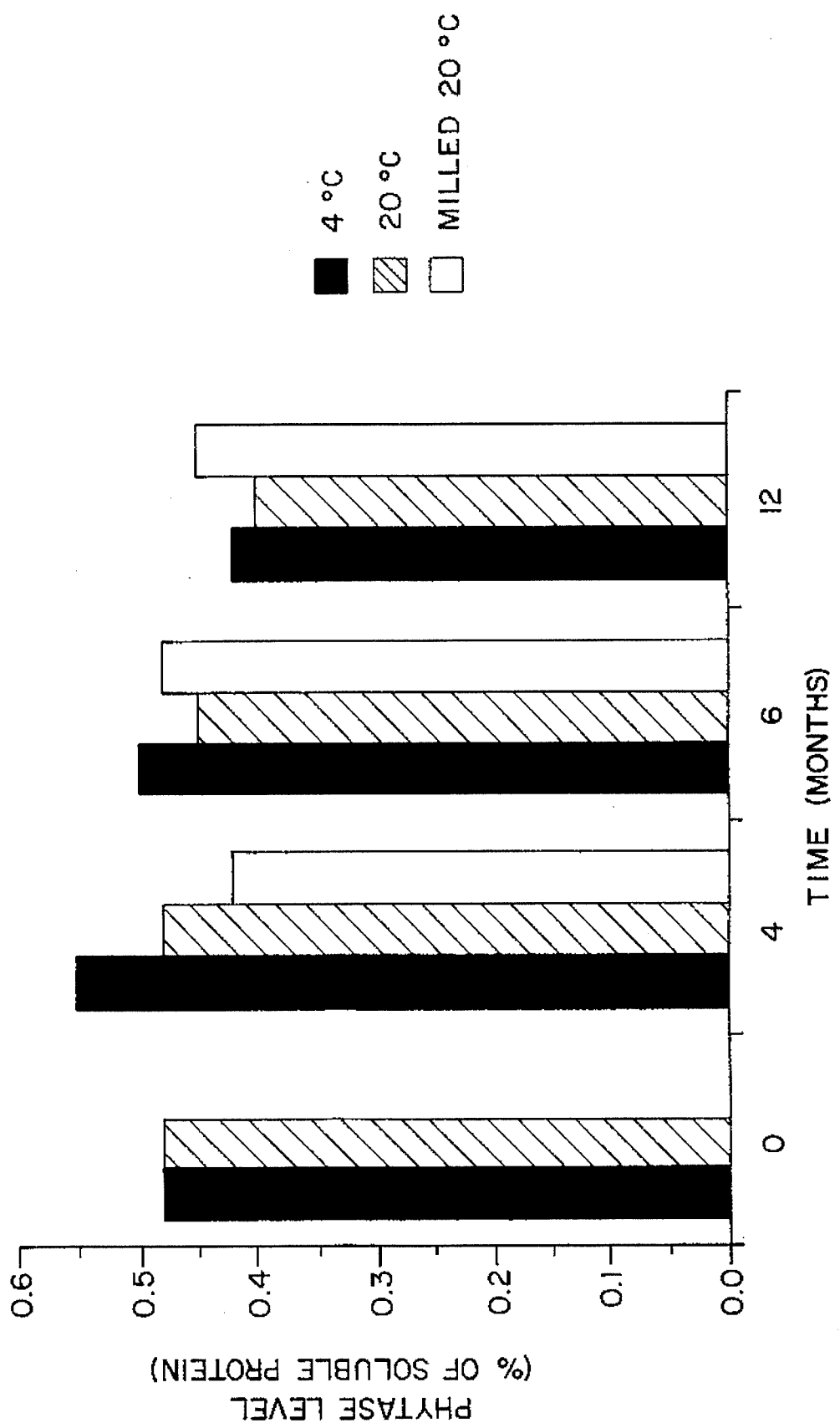
FIG. 14 is a histogram showing the storage stability of phytase produced in tobacco seeds.

Tobacco seeds of *Nicotiana tabacum* SR1 which has been transformed with the plasmid pMOG413 (see Example 6), in which phytase from *Aspergillus ficuum* was expressed extracellularly were stored at 4° C. and 20° C. Milled seeds were stored at 20° C. Phytase activity was determined at several time points. The enzyme appeared to be stable in unmilled, as well as in milled seeds (FIG. 14).

EXAMPLE 18

Expression of Phytase Under Control of the ACP Promoter a) Isolation of an 0.6 kb BamHI/HindIII fragment comprising the terminator sequences from the *Agrobacterium tumefaciens* nopalin synthase (NOS) and the CaMV 35S genes The oligonucleotide duplex TCV11/12 was cloned in the HindIII site of pMOG29 (see Example 4).

TCV11/12:
5' AGCTCTGCAGTGAGGTACCA3' (SEQ ID NO: 9)
3'     GACGTCACTCCATGGTTCGA5' (SEQ ID NO: 10)

The orientation of the adaptor TCV11/12 was checked by sequencing. A vector was used having the adaptor TCV11/12 in an orientation that would allow the cloning of the CaMV 35S terminator in a reverse orientation with respect to the *Agrobacterium tumefaciens* nopalin synthase (NOS) terminator sequence. In the resulting vector, linearized with PstI and KpnI, the 0.25 kb PstI/KpnI 35S terminator fragment isolated from plasmid pRT102 (Töpfer et al., 1987) was cloned. To destroy the PstI site, the obtained vector was linearized with PstI, blunted with Klenow polymerase, ligated and transformed to *E. coli*. From the resulting vector an 0.6 kb BamHI/HindIII fragment was isolated containing the terminator sequences from the *Agrobacterium tumefaciens* nopalin synthase (NOS) and the CaMV 35S genes, with the 35S terminator present in the reverse orientation.

b) Cloning and transformation of the binary vector

A 1 kb promoter of the seed-specific acyl carrier protein (ACP) gene from *Brassica napus* cv. Westar was synthesized by PCR as an EcoRI/NcoI fragment with isolated genomic DNA (Mettler, 1987) as a template. Synthetic DNA primers ACPI and ACPII, based on the sequence published by de Silva, J. et al. (1992) were used in the PCR reaction.

ACPI 5' CGCGAATTCTGCAGCCAGAAGGATAAA (SEQ ID NO: 11)
ACPII 5' GTGGTCGCCATGGTCGATATTCACG (SEQ ID NO: 12)

The EcoRI/NcoI fragment was cloned in pUC18, linearized with EcoRI and BamHI in a three-way ligation with the oligonucleotide duplex Trans1/2, encoding the signal peptide of the tobacco PR-S protein.

Trans 1/2:
5' CATGAACTTCCTCAAGAGCTTCCCCTTTTATGCCTTCCTTTGTTTTG       (SEQ ID NO: 13)
3'      TTGAAGGAGTTCTCGAAGGGGAAAATACGGAAGGAAACAAAA       (SEQ ID NO: 14)

GCCAATACTTTGTAGCTGTTACGCATGCTCGAG  3'       (SEQ ID NO: 15)
CCGGTTATGAAACATCGACAATGCGTACGAGCTCCTAG 5'    (SEQ ID NO: 16)

In the resulting vector, cut with SphI and BamHI, the phytase encoding cDNA fragment, isolated from pMOG417 (see Example 4) by digestion with SphI and BamHI (partial), was cloned. In this vector, linearized with BamHI (partial) and HindIII, an 0.6 kb DNA fragment containing the terminator sequences from the *Agrobacterium tumefaciens* nopalin synthase (NOS) and the CaMV 35S genes (with the 35S terminator present in the reverse orientation) was cloned.

Figure 15:
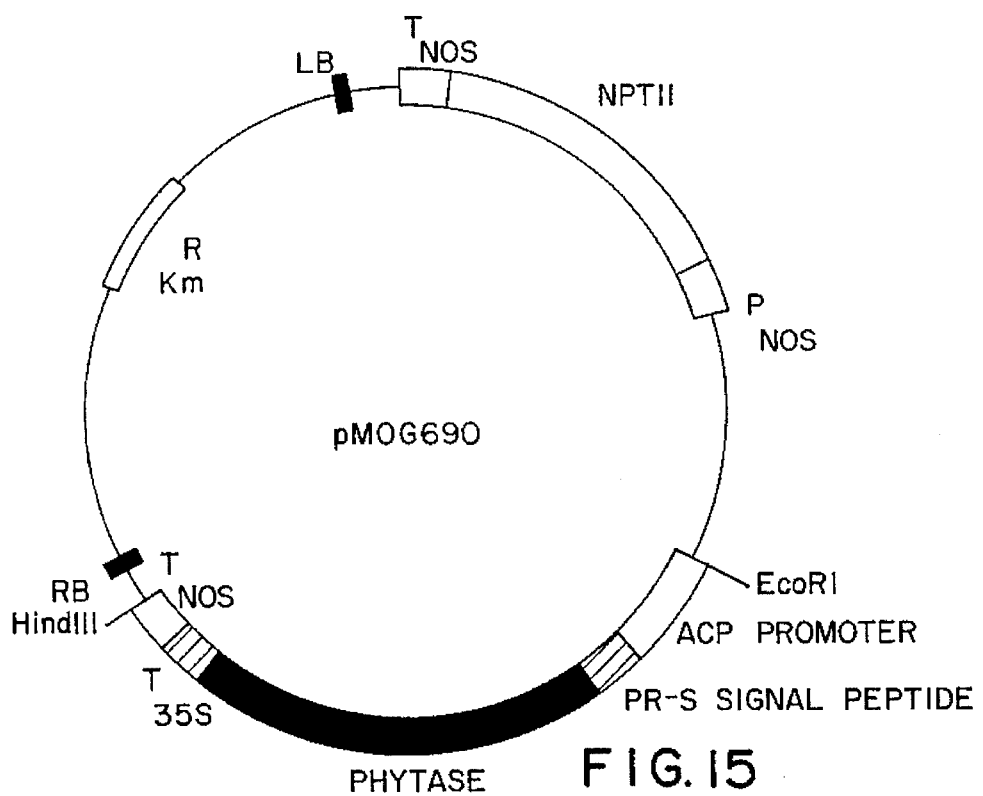
FIG. 15 is a diagram of plasmid pMOG690. Binary vector containing the phytase gene under control of the ACP promoter.

From the resulting vector, the 3.2 kb EcoRI/HindIII expression cassette was cloned into binary vector pMOG402 cut with EcoRI and HindIII. The resulting binary plasmid, designated pMOG690 (FIG. 15), was mobilized in a triparental mating with the *E. coli* strain HB101 containing plasmid pRK2013 (Ditta et al., 1980), into Agrobacterium strain MOG101, which contains a plasmid having the virulence genes necessary for T-DNA transfer to the plant (Hoekema et al., 1983). Tobacco was transformed as described (see Example 6). Transgenic seeds were harvested and assayed for phytase activity as described (see Example 10). The average expression level was 0.03% of soluble protein for 6 plants tested.

EXAMPLE 19

Expression of Phytase Under Control of a 3 kb Cruciferin Promoter

A 3 kb promoter fragment of a cruciferin gene of *Brassica napus* cv. Jet Neuf was used to control the expression of the phytase gene. The promoter fragment was fused to a DNA fragment encoding the AMV RNA4 leader, the tobacco PR-S signal peptide, mature phytase and the terminator sequences from the Agrobacterium nopalin synthase (NOS) and the CaMV 35S genes.

Isolated genomic DNA of *Brassica napus* cv. Jet Neuf was digested with SalI and BamHI, run on an agarose gel, blotted and hybridized with the PCR fragment comprising the 5' flanking region of the cruciferin A (cruA) gene (see Example 7). Southern hybridization showed a strongly hybridising fragment of about 2.8 kb. *Brassica napus* cv. Jet Neuf DNA, digested with SalI and BamHI was size-fractionated on a 10%–20% sucrose gradient. The fraction containing DNA fragments of approximately 2.5–3.2 kb was ligated in plasmid pGEM4 (Promega), linearized with SalI and BamHI. This ligation was transformed to *E. coli* strain DH10$^B$ (Gibco BRL), resulting in a partial genomic DNA library of about 100,000 clones. This library was screened with the PCR fragment of the cruA gene (see above) as a probe. One positive clone, designated pMOGcru, was found to contain a fragment that in the corresponding part was more than 95% identical with the cruA promoter sequence published by Ryan et al. (1989).

A set of synthetic oligonucleotides, TCV9 and TCV10 was used to synthesize by PCR technology a fragment consisting of the distal 13 bp of the cruA promoter from the PvuII site to the RNA start site followed by the RNA4 leader sequence of alfalfa mosaic virus (AMV) and the signal peptide-encoding sequence of the tobacco PR-S protein using plasmid pMOG417 (see Example 4) as a template.

TCV9  5' CAGAGCATGCGTAACAGCTAC                              3'   (SEQ ID NO: 17)
TCV10 5' CGGAATTCGGCAGCTGTAAGACCAGAGGGTTTTATTTTTA 3'   (SEQ ID NO: 18)

The thus-obtained 123 bp PCR fragment was cloned in a pGEM4 vector lacking the PvuII site (The PvuII site was destroyed by, in sequence, overdigestion of pGEM4 with PvuII, ligation, digestion with PvuII, transformation to *E. coli*, and screening for clones lacking the PvuII site), linearized with EcoRI and SphI. The resulting vector was linearized with EcoRI and PvuII, and used in a three-way ligation containing additionally a 0.1 kb SalI/PvuII cruA promoter fragment from plasmid pMOG428 (see Example 7) and the 2.8 kb EcoRI/SalI cruciferin promoter fragment from pMOGcru (see above). In the obtained vector, cut with SphI and BamHI, the 1.5 kb cDNA fragment from pMOG417 encoding phytase (see Example 4), obtained by digestion with SphI and BamHI (partial), was cloned. In the resulting vector, linearized with BamHI (partial) and HindIII, an 0.6 kb DNA fragment consisting of the terminator sequences from the Agrobacterium nopalin synthase (NOS) and the CaMV 35S genes was cloned. The CaMV 35S terminator was present in the reverse orientation (see Example 18). The 5.2 kb expression cassette was cut out with EcoRI and HindIII (partial), and cloned into binary vector pMOG402 cut with EcoRI and HindIII.

Figure 16:
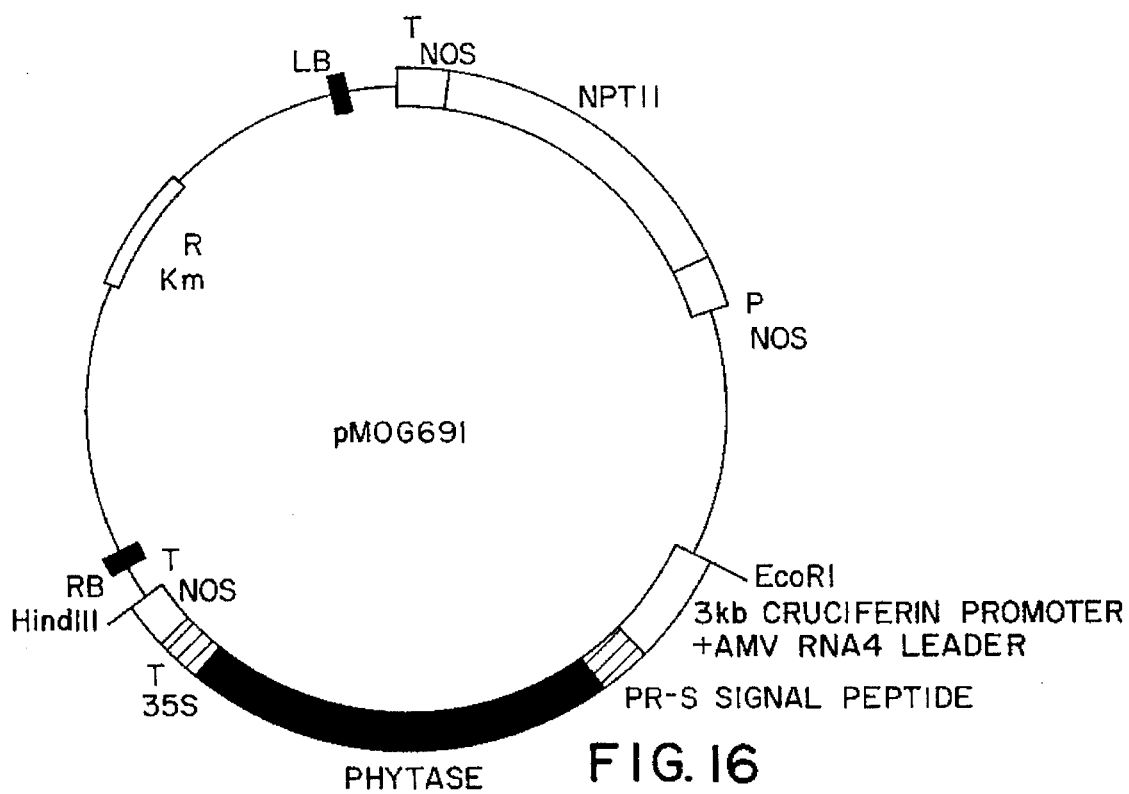
FIG. 16 is a diagram of plasmid pMOG691 containing the phytase gene under control of a 3 kb cruciferin promoter.

The resulting binary plasmid, designated pMOG691 (FIG. 16), was mobilized in a triparental mating with the *E. coli* strain HB101 containing plasmid pRK2013 (Ditta et al., 1980), into Agrobacterium strain MOG101, which contains a plasmid having the virulence genes necessary for T-DNA transfer to the plant (Hoekema et al., 1983). Tobacco was transformed as described (see Example 6). Transgenic seeds were harvested and assayed for phytase activity as described (see Example 10). The average expression level was 0.3% of soluble protein for 9 plants tested.

While the present invention has been described with reference to specific embodiments thereof, it should be understood by those skilled in the art that various changes may be made and equivalents may be substituted without parting from the true spirit and scope of the invention. In addition, many modifications may be made to adapt a particular situation, material, plant, seed, process, process step or steps to the object, spirit and scope of the invention. All such modifications are intended to be within the scope of the claims appended hereto.

REFERENCES

Altenbach, S. B., Pearson, K. W., Meeker, G., Staraci, L. C. & Sun, S. S. M. (1989) Plant Mol. Biol. 13, 513.

Auffray & Rougeon (1980) Eur. J. Biochem. 107, 303–314.

Barker, S. J., Harada, J. J. & Goldberg, R. B. (1988) Proc. Natl. Acad. Sci. USA 85, 458.

Baulcombe, D. C., Saunders, G. R., Bevan, M. W., Mayo, M. A. & Harrison, B. D. (1986) Nature 321, 446.

Bäumlein, H., Wobus, U., Pastell, J., & Kafatos, F. C. (1986) Nucl. Acids Res. 14, 2707.

Beachy, R. N., Chen, Z.- L., Horsch, R. B., Rogers, S. G., Hoffmann, N. J. & Fraley, R. T. (1985) EMBO J. 4, 3047.

Bevan, M. (1984) Nucl. Acids Res. 12, 8711.

Brederode, F. T., Koper-Zwarthoff, E. C. & Bol, J. F. (1980) Nucl. Acids Res. 8, 2213.

Bustos, M. M., Guiltinan, M. J., Jordano, J., Begum, D., Kalkan, F. A. & Hall, T. C. (1989) Plant Cell 1, 839.

Casey, R. & Domoney, C. (1987) Plant Mol. Biol. Reporter 5, 261.

Chee, B. B., Klassy, R. C. & Slightom, J. L. (1986) Gene 41, 47.

Cornelissen, B. J. C., Hooft van Huijsduijnen, R. A. M. & Bol, J. F. (1986) Nature 321, 531.

Della-Cioppa, G., Kishore, G. M., Beachy, R. N. & Fraley, R. T. (1987) Plant Physiol. 84, 965.

de Silva, J. et al. (1992) Mol. Biol. 18, 1163–1172.

Ditta, G., Stanfield, S., Corbin, D. & Helinski, D. R. (1980) Proc. Natl. Acad. Sci. USA 77, 7347.

Dorel, C., Voelker, T. A., Herman, E. M. & Chrispeels, M. J. (1989) J. Cell Biol. 108, 327.

Doyle, J. J., Schuler, M. A., Godette, W. D., Zenger, V., Beachy, R. N. & Slightom, J. L. (1986) J. Biol. Chem. 261, 9228.

Ellis, J. R., Shirsat, A. H., Hepher, A., Yarwood, J. N., Gatehouse, J. A., Croy, R. R. D. & Boulter, D. (1988) Plant Mol. Biol. 10, 203.

Fischer, R. L. & Goldberg, R. B. (1982) Cell 29, 651.

Fry, J. & Barnason, A. & Horsch, R. B. (1987) Plant Cell Reports 6, 321.

Gasser, C. S. & Fraley, R. T. (1989) Science 244, 1293.

Goodman, R. M., Knauf, V. C., Houck, C. M. & Comai, L. (1987) PCT/WO 87/00865.

Gordon-Kamm, W. J., Spencer, T. M., Mangano, M. L., Adams, T. R., Daines, R. J., Start, W. G., O'Brien, J. V., Chambers, S. A., Adams Jr., W. R., Willets, N. G., Rice, T. B., Mackey, C. J., Krueger, R. W., Kausch, A. P. & Lemaux, P. G. (1990) The Plant Cell 2, 603.

Guilley, H., Dudley, R. K., Jonard, G., Balazs, E. & Richards, K. E. (1982) Cell 30, 763.

Harada, J. J., Barker, S. J. & Goldberg, R. B. (1989) Plant Cell 1, 415.

Hattori, T., Nakagawa, T., Maeshima, M., Nakamura, K., & Asahi, T. (1985) Plant Mol. Biol. 5, 313.

Hiatt, A., Cafferkey, R. & Boedish, K. (1989) Nature 342, 76.

Higgins, T. J. V., (1984) Annu. Rev. Plant Physiol. 35, 191.

Higgins, T. J. V., Newbigin, E. J., Spencer, D., Llewellyn, D. J. & Craig, S. (1988) plant Mol. Biol. 11, 683.

Hoekema, A., Hirsch, P. R., Hooykaas, P. J. J. & Schilperoort, R. A. (1983) Nature 303, 179.

Hoffman, L. M., Donaldson, D. D., Bookland, R., Rashna, K. & Herman, E. M. (1987) EMBO J. 6, 3213.

Horsch, R. B., Fry, J. E., Hoffmann, N. L., Eichholtz, D., Rogers, S. G. & Fraley, R. T. (1985) Science 227, 1229.

Iturriaga, G., Jefferson, R. A. & Bevan, M. W. (1989) Plant Cell 1, 381.

Jefferson, R. A. (1987) Plant Mol. Biol. Reporter 5, 387.

Jordano, J., Almoguera, C. & Thomas, T. L. (1989) Plant Cell 1, 855.

Kay, R., Chan, A., Dayly, M. & McPherson, J. (1987) Science 236, 1299.

Klee, H., Horsch, R. & Rogers, S. (1987) Annu. Rev. Plant Physiol. 38, 467.

Krebbers, E. & Vandekerckhove, J. (1990) TIBTECH, 8, 1.

Larkins, M. A. (1981) In: *The biochemistry of plants* Vol. 6 (Academic Press, San Diego: Stumpf, P. K. & Conn, E. E., eds.). Chapter 11. p. 471.

Lee, B., Murdoch, K., Topping, J., Kreis, M. & Jones, M. G. K. (1989) Plant Mol. Biol. 13, 21.

Lycett, G. W., Delauney, A. J., Gatehouse, J. A., Gilroy, J., Croy, R. R. D. & Boulter, D. (1983) Nucl. Acids Res. 11, 2367.

Lycett, G. W., Croy, R. R. D., Shirsat, A. H. & Boulter, D. (1984) Nucl. Acids Res. 12, 4493.

Mariani, C., de Beuckeleer, M., Truettner, J., Leemans, J., & Goldberg, R. B. (1990) Nature 347, 737.

Marsh, J. L., Erfle, M. & Wykes, E. J. (1984) Gene 32, 481.

Mettler, I. J. (1987) Plant Mol. Biol. Rep. 5, 346.

Okamura, J. K., Jokufu, K. D. & Goldberg, R. B. (1986) Proc. Natl. Acad. Sci. USA 83, 8240.

Pang, P. P., Pruitt, R. E. & Meyerowitz, E. M. (1988) Plant Mol. Biol. 11, 805.

Potrykus, I. (1990) Bio/Technol. 8, 535.

Radke, S. E., Andrews, B. M., Moloney, M. M., Crough, M. L., Kridl, J. C. & Knauf, V. C. (1988) Theor. Appl. Genet. 75, 685.

Reilly, P. J. (1985) In: *Starch Conversion Technology* (Marcel Dekker, Inc., New York: Van Beynum, G. M. A. & Roels, J. A., eds.), Chapter 5, p. 101.

Riggs, C. D., Hunt, D. C., Lin, J. & Chrispeels, M. J. (1989) Plant Sci. 63, 47.

Rodenburg, K. W., DeGroot, M. J. A., Schilperoort, R. A. & Hooykaas, P. J. J. (1989) Plant Mol. Biol., 13, 711.

Ryan, A. J., Royal, C. L., Hutchinson, J. & Shaw, C. H. (1989) Nucl. Acids Res. 17, 3584.

Scofield, S. R. & Crouch, M. L. (1987) J. Biol. Chem. 262, 12202.

Schilperoort, R. A., Hoekema, A. & Hooykaas, P. J. J. (1984) European Patent Application No. 0 120 516.

Sengupta-Gopalan, C., Reichert, N. A., Barker, R. F., Hall, T. C. & Kemp, J. D. (1985) Proc. Natl. Acad. Sci. USA 82, 3320.

Shimamoto, K., Terada, R., Izawa, T. & Fujimoto, H. (1989) Nature 338, 274.

Shotwell, M. A. & Larkins, B. A. (1989) In: *The biochemistry of plants* Vol. 15 (Academic Press, San Diego: Stumpf, P. K. & Conn, E. E., eds.). Chapter 7. p. 297.

Sijmons, P. C., Dekker, B. M. M., Schrammeijer, B., Verwoerd, T. C., van den Elzen, P. J. M. & Hoekema, A. (1990) Bio/Technol. 8, 217.

Slightom, J. L., Schaber, M. D. & Kramer, R. A. (1986) In: *Molecular biology of seed storage proteins and lectins* (Waverley Press, Baltimore: Shannon, L. M. & Chrispeels, M. J., eds.) Am. Soc. Plant Physiol. p. 183.

Smith, J. J. & Raikhel, N. V. (1989) Plant Mol. Biol. 13, 601.

Töpfer et al. (1987) Nucl. Acids Res. 15, 5890.

Vaara, T., Vaara, M., Simell, M., Lehmussaari, A. & Caransa, A. (1989) European Patent Application 0 321 004.

Vandekerckhove, J., VanDamme, J., VanLijsebettens, M., Botterman, J., DeBlock, M., DeClerq, A., Leemans, J., Van Montagu, M. & Krebbers, E. (1989) Bio/Technol. 7, 929.

van Gorcom, R. F. M., van Hartingsveldt, W., van Paridon, P. A., Veenstra, A. E., Luiten, R. G. M., Selten, G. C. M. (1991) European Patent Application 89202436.5, Publication No. 0 420 358, filed Sep. 27, 1989.

Vasil, V., Redway, F. & Vasil, I. K. (1990) Bio/Technol. 8, 429.

Vitale, A. & Bollini, R. (1986) In: *Molecular biology of seed storage proteins and lectins* (Waverley Press, Baltimore: Shannon, L. M. & Chrispeels, M. J., eds.) Am. Soc. Plant Physiol. p. 175.

Voelker, T. A., Herman, E. M. & Chrispeels, M. J. (1989) Plant Cell 1, 95.

Vonder Haar, R. A., Allen, R. D., Cohen, E. A., Nessler, C. L. & Thomas, T. L. (1988) Gene 74, 433.

We claim:

1. A method to effect the conversion of substrates to products in an enzyme-catalyzed reaction which method comprises adding to a reaction mixture containing said substrates the seeds of a transgenic plant, wherein said plant has been modified to contain an expression system for the production of said enzyme, and wherein the enzyme is heterologous to the seed.

2. A method to effect the conversion of substrates to products in an enzyme-catalyzed reaction which method comprises adding to a reaction mixture containing said substrates the seeds of a transgenic plant, wherein said plant has been modified to contain an expression system for the production of said enzyme, and wherein the reaction mixture would not otherwise contain any seeds.

3. The method of claim 1 or 2 wherein the seeds are in milled form.

4. The method of claim 3 wherein the seeds are milled prior to said adding.

5. The method of claim 1 or 2 wherein said seeds are milled subsequent to said adding.

6. The method of claim 1 or 2 wherein the enzyme is a hydrolase enzyme.

7. The method of claim 6 wherein the hydrolase enzyme is a protease, a cellulase, a hemicellulase, a phosphatase, a lipase, a pectinase, an amylase, a lysozyme, a pellulanase, a phytase or a chitinase.

8. The method of claim 1 or 2 wherein the enzyme is a lyase.

9. The method of claim 8 wherein the lyase is pectinase.

10. The method of claim 1 or 2 wherein the enzyme is an isomerase.

11. The method of claim 10 wherein the isomerase is a glucose isomerase.

12. The method of claim 1 or 2 wherein said reaction is a digestive reaction and the seeds are added to the reaction mixture by adding said seeds to an animal food.

13. A reaction mixture containing the substrate of an in vitro enzyme-catalyzed reaction, which mixture further comprises seeds of a transgenic plant modified to contain an expression system for production of said enzyme in the seeds of the plant, wherein said enzyme is heterologous to said seeds.

14. A reaction mixture containing the substrate of an in vitro enzyme-catalyzed reaction, which mixture further comprises seeds of a transgenic plant modified to contain an expression system for production of said enzyme in the seeds of the plant and wherein said reaction mixture would otherwise not contain seed.

15. An animal feedstuff which comprises the seeds of a transgenic plant modified to contain an expression system for production in its seeds of an enzyme effective in aiding digestion of a substrate further contained in the feedstuff.

* * * * *